United States Patent
Zhu et al.

(10) Patent No.: US 6,228,631 B1
(45) Date of Patent: May 8, 2001

(54) RECOMBINANT α-N-ACETYLGALACTOSAMINIDASE ENZYME AND CDNA ENCODING SAID ENZYME

(75) Inventors: Alex Zhu; Jack Goldstein, both of New York, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/070,356

(22) Filed: Apr. 30, 1998

Related U.S. Application Data

(63) Continuation of application No. 08/396,880, filed on Mar. 1, 1995, now abandoned, which is a continuation of application No. 08/037,248, filed on Mar. 26, 1993, now abandoned, which is a continuation-in-part of application No. 07/964,756, filed on Oct. 22, 1992, now abandoned.

(51) Int. Cl.[7] ............... C12N 9/40; C12N 9/24; C12N 15/56; C12N 5/10; C12N 15/63
(52) U.S. Cl. .......... 435/208; 435/200; 435/320.1; 435/325; 435/252.3; 536/23.2
(58) Field of Search .................. 435/200, 208, 435/320.1, 325, 252.3; 536/23.2

(56) References Cited

U.S. PATENT DOCUMENTS 4,609,627 * 9/1986 Goldstein ............... 435/269
5,610,063 3/1997 Smith ............... 435/254.23

OTHER PUBLICATIONS

A.M. Wang et al. "Human Alpha–N–Acetylgalactosaminidase Molecular Cloning, Nucleotide Sequence, and Expression of a Full Length cDNA", J. Biol. Chem. 265(35): 21859–21866, Dec. 1990.*

J. Hata et al., "Purification and characterization of N–acetyl–alpha–D–galactosaminidase from *Gallus domesticus*" 1992 Biochemistry International 28(1):77–86.

E. Hogan et al., "Membrane glycosphingolipids in chicken muscular dystrophy" 1982 Adv. Exp. Med. Biol. 152:273–278.

* cited by examiner

*Primary Examiner*—Rebecca E. Prouty
(74) *Attorney, Agent, or Firm*—Wolf, Greenfield & Sacks P.C.

(57) ABSTRACT

This invention relates to a recombinant enzyme for use in the removal of A antigens from the surface of cells in blood products. Specifically, this invention is directed to a recombinant α-N-acetylgalactosaminidase enzyme from chicken liver, methods of cloning and expressing said recombinant α-N-acetylgalactosaminidase enzyme and a method of removing A antigens from the surface of cells in blood products using said recombinant α-N-acetylgalactosaminidase enzyme.

10 Claims, 6 Drawing Sheets

```
ATG CTG GAG AAC GGG CTG GCG CGG ACC CCG CCC ATG GGC TGG TTG GCC      48
Met Leu Glu Asn Gly Leu Ala Arg Thr Pro Pro Met Gly Trp Leu Ala

TGG GAG CGG TTC CGC TGC AAC GTG AAC TGC CGG GAG GAC CCC CGC CAG      96
Trp Glu Arg Phe Arg Cys Asn Val Asn Cys Arg Glu Asp Pro Arg Gln

TGC ATC AGT GAG ATG CTC TTC ATG GAG ATG GCA GAC CGA ATA GCA GAG     144
Cys Ile Ser Glu Met Leu Phe Met Glu Met Ala Asp Arg Ile Ala Glu

GAC GGC TGG AGG GAG CTG GGC TAC AAG TAC ATC AAT ATC GAT GAC TGC     192
Asp Gly Trp Arg Glu Leu Gly Tyr Lys Tyr Ile Asn Ile Asp Asp Cys

TGG GCC GCC AAG CAG CGT GAC ACT GAG GGG CGG CTG GTG CCT GAC CCC     240
Trp Ala Ala Lys Gln Arg Asp Thr Glu Gly Arg Leu Val Pro Asp Pro

GAG AGG TTC CCC CGG GGC ATT AAG GCC TTG GCT GAC TAC GTT CAT GCC     288
Glu Arg Phe Pro Arg Gly Ile Lys Ala Leu Ala Asp Tyr Val His Ala

CGA GGC TTG AAG CTG GGC ATT TAT GGC GAC CTG GGC AGA CTC ACC TGT     336
Arg Gly Leu Lys Leu Gly Ile Tyr Gly Asp Leu Gly Arg Leu Thr Cys

GGA GGC TAC CCA GGC ACC ACG CTG GAC CGT GTG GAG CAG GAC GCA CAG     384
Gly Gly Tyr Pro Gly Thr Thr Leu Asp Arg Val Glu Gln Asp Ala Gln

ACC TTC GCT GAG TGG GGT GTG GAC ATG CTG AAG CTA GAT GGG TGC TAC     432
Thr Phe Ala Glu Trp Gly Val Asp Met Leu Lys Leu Asp Gly Cys Tyr

TCA TCG GGG AAG GAG CAG GCA CAG GGC TAC CCA CAA ATG GCA AGG GCC     480
Ser Ser Gly Lys Glu Gln Ala Gln Gly Tyr Pro Gln Met Ala Arg Ala

TTG AAC GCC ACT GGC CGC CCC ATC GTC TAC TCC TGC AGC TGG CCA GCC     528
Leu Asn Ala Thr Gly Arg Pro Ile Val Tyr Ser Cys Ser Trp Pro Ala

TAC CAG GGG GGG CTG CCT CCC AAG GTG AAC TAC ACT CTC CTG GGT GAG     576
Tyr Gln Gly Gly Leu Pro Pro Lys Val Asn Tyr Thr Leu Leu Gly Glu

ATC TGC AAC CTG TGG CGG AAC TAC GAT GAC ATC CAG GAC TCA TGG GAC     624
Ile Cys Asn Leu Trp Arg Asn Tyr Asp Asp Ile Gln Asp Ser Trp Asp

AGC GTG CTT TCC ATC GTG GAC TGG TTC TTC ACA AAC CAG GAT GTG CTG     672
Ser Val Leu Ser Ile Val Asp Trp Phe Phe Thr Asn Gln Asp Val Leu

CAG CCG TTT GCT GGC CCT GGC CAC TGG AAT GAC CCA GAC ATG CTC ATC     720
Gln Pro Phe Ala Gly Pro Gly His Trp Asn Asp Pro Asp Met Leu Ile

ATT GGA AAT TTC GGT CTC AGC TAT GAG CAG TCA CGT TCC CAA ATG GCC     768
Ile Gly Asn Phe Gly Leu Ser Tyr Glu Gln Ser Arg Ser Gln Met Ala

TTG TGG ACC ATT ATG GCA GCT CCA CTC CTC ATG TCC ACC GAC CTG CGC     816
Leu Trp Thr Ile Met Ala Ala Pro Leu Leu Met Ser Thr Asp Leu Arg

ACT ATC TCG CCG AGT GCC AAG AAG ATT CTG CAG AAC CGC CTG ATG ATC     864
Thr Ile Ser Pro Ser Ala Lys Lys Ile Leu Gln Asn Arg Leu Met Ile

CAG ATA AAC CAG GAC CCC TTG GGA ATC CAG GGG CGC AGG ATC ATC AAG     912
Gln Ile Asn Gln Asp Pro Leu Gly Ile Gln Gly Arg Arg Ile Ile Lys

GAG GGA TCC CAC ATT GAG GTG TTC CTG CGC CCG CTG TCA CAG GCT GCC     960
Glu Gly Ser His Ile Glu Val Phe Leu Arg Pro Leu Ser Gln Ala Ala

AGT GCC CTG GTC TTC TTC AGC CGG AGG ACA GAC ATG CCC TTC CGC TAC    1008
Ser Ala Leu Val Phe Phe Ser Arg Arg Thr Asp Met Pro Phe Arg Tyr

ACC ACC AGT CTT GCC AAG CTT GGC TTC CCC ATG GGA GCT GCA TAT GAG    1056
Thr Thr Ser Leu Ala Lys Leu Gly Phe Pro Met Gly Ala Ala Tyr Glu
```

FIG. 2A

```
GTG CAA GAC GTG TAC AGT GGG AAG ATC ATC AGT GGC CTG AAG ACA GGA  1104
Val Gln Asp Val Tyr Ser Gly Lys Ile Ile Ser Gly Leu Lys Thr Gly
GAC AAC TTC ACA GTG ATC ATC AAC CCC TCA GGG GTG GTG ATG TGG TAC  1152
Asp Asn Phe Thr Val Ile Ile Asn Pro Ser Gly Val Val Met Trp Tyr
CTG TGT CCC AAA GCA CTG CTC ATC CAG CAG CAA GCT CCT GGG GGG CCC  1200
Leu Cys Pro Lys Ala Leu Leu Ile Gln Gln Gln Ala Pro Gly Gly Pro
TCG CGC CTG CCC CTT CTG TGA GGC CCA TGA TTG GGA GCC CTG GGA TAC  1248
Ser Arg Leu Pro Leu Leu ***
ATC TCA CCG CTG CTC AAG TGC CTT CTT CTG GTG TGG CTG GGG GAG GAC  1296
ATG CAG CTT GCT CCT CTG GCA CCA CCT GAT GAT TTC TAC TCA TTC CAC  1344
GTG AAG CAG GAC TTC TTG TTA CTC CCT CCT GAG AGC ATG CAA AGC GCT  1392
CTG AGG TCC TCC TGT GGA AGA GGA GTG TTC CCA GTG ACC ATC CTT TAG  1440
GAC CAG ATG TGG TCA CCT TTT TTC CTT TGC TTG GCT TAG GAC AAA GGG  1488
CTG TCC ACA GGC TGC ACC CCT CTT CCC AGG CAC CAT CCC CAG ACC AGG  1536
AGC TCC TGG GGC CAG GCT GTC TCT GTC TGG CAG CAG GAT CAG CAG GTA  1584
ACA CCA CTA CAG TGT AGT CCG CAC ATA ATG AAA AAG AAA TCT AAA CAA  1632
AAC GTG TGC CAG TAG TGT ACT GAA CCC GCT CTG GTT ACA GCA GAG CAA  1680
AAC CTG AGT TGT CCA TGC ACA ATC CCA GTA TCC TCA CTG TGG TGT TAG  1728
CAT GAA AAA TTG CAG TCA CAG TGC ATT GTG CAC GAG TGG TGT CTG GAA  1776
GAT GCT GAT GCT TGT TCG TGG TGG TCT TAA GGT GGG AGA TGC TCA TGG  1824
GTG CTG GCC AAG TTG CAT CTC AAT CTT GTG AGG CTG AAC CTT CCA GCA  1872
TTT CTC AGG GAA AGG CTC TTC CTT TTA AAG GCA GCC TGC ACA AAT AGA  1920
AGG GGC TCA GAA GGA CGC ACG AGG AGG GGC TCA GGT GGG CCG TGC TCC  1968
CCT GAC CAC CCC AAG AGG GGT CAA CTA CTC ACC AAA ATC TAC CCC TTT  2016
CAA GGC CAG GTC AGC CCA GGG AGA CGC ACC CAA GGT TAA ACC TCA AAA  2064
CAG GAA ATC ACC CTA TTT TAA ATT AGT GAG AAA TTG AAC TTC CCC ATT  2112
CTA TTC AGA TGA GGG CTA GAA GCC CAC TCT CCT TAG AAG GCA CGT GGT  2160
GGA TTC CTG CCC CTT GCA GAG ACA TTG TGG TCT GAA GCA AGA TGC TGA  2208
ATG TGA TCT TTG CAG CGC TGG AAA TGA CAT GTC TGT TTC ATG CTT GTG  2256
TGG GAG ATG GCT TTG TTT TTG TGA TTT TGA CAA TTT AAC TGA AAT AAA  2304
AGG GAA GCA GAG GGG                                              2319
```

FIG. 2B

```
              20                    40                              60
I                                              MLENGLARTPPMGWLAWERFRCNVN
II                          MLLKTVLLLGHVAQVLMLDNGLLQTPPMGWLAWERFRCNIN
III            MQLRNPELHLGCALALRFLALVSWDIPGARALDNGLARTPTMGWLHWERFMCNLD
IV                      MFAFYFLTACISLKGVFGVSPSYNGLGLTPQMGWDNWNTFACDV
V       MATHYSIIGGMIIVVLLMIIGSEGGRLLEKKNRTSAEAEHYNVRRYLAENGLGQTPPMGWNSWNHFGCDIN
VI                 MIQGLESIMNQGTKRILLAATLAATPWQVYGSIEQPSLLPTPPMGFNNWARFMCDLN 80                  100                   120                140
I       CREDPRQCISEMLFMEMADRIAEDGWRELGYKYINIDDCWAAKQRDTEGRLVPDPERFPRGIKALADYVHAR
II      CDEDPKNCISEQLFMEMADRMAQDGWRDMGYTYINIDDCWIGG RDASGRLMPDPKRFPHGIPFLADYVHSL
III     CQEEPDSCISEKLFMEMAELMVSEGWKDAGYEYLQIDDCWMAPQRDSEGRLQADPQRFPHGIRQLANYVHSK
IV                 SEQLLIDTADRISDLGLKDMGYKYIILDDCWSSG RDSDGFLVADEQKFPNGMGHVADHLHNN
V                  ENVVRETADAMVSTGLAALGYQYINLDDCWAELNRDSEGNMVPNAAAFPSGIKALADYVHSK
VI                 ETLLFTETADIMAANGLRDAGVNRINLDDCWMAYQRSDNGSLQWNTTKFPHGLPWLAKYVKAK 160                    180                    200
I       GLKLGIYGDLGRLTCG GYPGTTLDRVEQDAQTFAEWGVDMLKLDGCYSSGKEQ       AQGVPQMARAL
II      GLKLGIYADMGNFTCM GYPGTTLDKVVQDAQTFAEWKVDMLKLDGCFSTPEER       AQGVPKMAAAL
III     GLKLGIYADVGNKTCA GFPGS FGYYDIIDAQTFADWGVDLLKFDGCVCDSLEN       LADGVKHMSLAL
IV      SFLFGMYSSAGEYTCA GYPGS LGREEEDAQFFANNRVDYLKYDNCYNKGQFG      TPEISYHRVKAMSDAI
V       GLKLGVYSDAGNQTCSKRMPGS LGHEEQDAKTFASWGVDYLKYDNCENLGISV        KERVPPMGKAL
VI      GFHFGIYEDSGNMTCG GYPGS YNHEEQDANTFASWGIDYLKLDGCNVYATQGRTLEEEYKQRVGHWHQVL 220                   240                260                280
I       NATGRPIMYS CSWPAYQGGLPPKVNYTLLGEIQNLWRNYDDIQDSWDSVLSIVDWFFTNQDVLQPF
II      NATGRPIAFS CSWPAYEGGLPPRVNYSLLADIQNLWRNYDDIQDSWWSVLSILNWFVEHQDILQPV
III     NRTGRSIMYS CEWPLYMWPFQ KPNYTEIRQYQNLWRNFADIDDSWKSIKSILDWTSFNQERIVDV
IV      NKTGRPIFYSLQNWGQDLTFYWGSGIA           NSWRMSGDVTAEFTRPDSRCPCDGDEYDCKYAGFHCSI
V       LSSGRPIFFSMCEWGWEDPQIWAKSIG           NSWRTTGDIEDNWNSMTSIADSNDKWASY
VI      SKMQHPLIFSESAFAYFAGTDNNTDWYTVMDWVPIYGELARHSTDILVYSGAGSAWDSIMNNY 300                  320                   340
I            AGPGHWNDPDMLIIGNFGLSYEQSRSQMALWTIMAAPLLMSTDLRTISPSAKKILQNRL
II           AGPGHWNDPDMLLIGNFGLSIEQSRAQMALWTVLAAPLLMSTDLRTISAQNMDILQNPL
III          AGPGGWNDPDMLIVGNFGLSWNQQVTQMALWAIMAAPLFMSNDLRHISPQAKALLQDKD
IV      MNILNKAAPMGQNAGVGGWNDLDNLEVGVGNLTDDEEKAHFSMWAMVKSPLIIGANVNNLKASSYSIVSQAS
V            AGPGGWNDPDMLEVGNGGMTIEEYRSHFSIWAIAKAPLLVGCDIRAMDDTTHELISNAE
VI      NYNTLLARYQRPGYFNDPDFLIPDHPGLTADEKRSHFALWASFSAPLIISAYUPALSKDEIAFLINEA 360                  380                    400                   420
I       MIQINQDPLGIQGRRIIKEGSHIEVFLRPLSQAASALVFFSRRT DMPFRYTTSLAKLGFPMGAAYEV      Q
II      MIKINQDPLGIQGRRIHKEKSLIEVYMRPLSNKASALVFFSCRT DMPYRYHSSLGQLNFTGSIVYEA      Q
III     IVAINQDPLGKDGYQLI RQGDNFEVWERPLSGLAWAVAMINRQEIGGPRSYTIAVASLGKGVACNPACFITQ
IV      IVAINQDSNGIPATRVWRYYVSDTDEYGQGEIQMWSGPLDNGDQVVALLNGGSVSRPMNTTLEEIFFDSNLG
V       IVAVNQDKLGVQGKKV KSTNDLEVWAGPLSDNKVAVILWNRSSSRATVTASWSDIGLQQGTTVDARDLWEH
VI      LIAVNQDPLAQQATLASRDDTLDILTRSLANGDRLLTVLNKGNTTVTRDIPVQWLGLTETDCTYTAEDLWDG 440                   460                  480
I       DVYSGKIISGLKTGDNFTIVINPSGVVMWYLCPKALLIQQQAPGGPSRLPLL
II      DVYSGDIISGLRDETNFTIVINPSGVVMWYLYPIKNLEMSQQ
III     LLPVKRKLGFYEWTSRLRSHINPTGTVLLQLENTMQMSLKDLL
IV      SKKLTSTWDIYDLWANRVDNSTASAILGRNKTATGILYNATEQSYKDGLSKNDTR**
V       STQSLVSGEISAEIDSHACKMYVLTPRS
VI      KTQKISDHIKIELASHATAVFRLSLPQGCSSVVPTGLVFNTASGNCLTAASNSSV**
```

RECOMBINANT α-N-ACETYLGALACTOSAMINIDASE ENZYME AND CDNA ENCODING SAID ENZYME

CROSS REFERENCE TO RELATED APPLICATIONS

This is a continuation of U.S. application Ser. No. 08/396,880, filed Mar. 1, 1995 now abandoned, which is a continuation of U.S. application Ser. No. 08/037,248, filed Mar. 26, 1993 now abandoned, which is a continuation-in-part of U.S. application Ser. No. 07/964,756, filed Oct. 22, 1992 now abandoned, the contents of which are hereby incorporated by reference.

STATEMENT OF GOVERNMENT INTEREST

This invention was made with government support under NMRDC Grant Number N0014-90-J-1638. As such, the government has certain rights in the invention.

FIELD OF THE INVENTION

This invention relates to a recombinant enzyme for use in the removal of type A antigens from the surface of cells in blood products, thereby converting certain sub-type A blood products to type O blood products and certain type AB blood products to type B blood products. This invention further relates to methods of cloning and expressing said recombinant enzyme. More particularly, this invention is directed to a recombinant chicken liver α-N-acetylgalactosaminidase enzyme, methods of cloning and expressing said recombinant α-N-acetylgalactosaminidase enzyme, and a method of removing type A antigens from the surface of cells in type A and AB blood products using said recombinant α-N-acetylgalactosaminidase enzyme by contacting said enzyme with blood products so as to remove the terminal moiety of the A-antigenic determinant from the surface of cells (for example, erythrocytes) in said blood products, while allowing the structure and function of the cells in the blood products to remain intact. The recombinant α-N-acetylgalactosaminidase enzyme of this invention provides a readily available and cost-efficient enzyme which can be used in the removal of type A antigens from the surface of cells in type A and AB blood products. Treatment of certain sub-type A blood products with the recombinant enzyme of this invention provides a source of cells free of the A antigen, which blood products are thereby rendered useful in transfusion therapy in the same manner of O type blood products.

BACKGROUND OF THE INVENTION

As used herein, the term "blood products" includes whole blood and cellular components derived from blood, including erythrocytes (red blood cells) and platelets.

There are more than thirty blood group (or type) systems, one of the most important of which is the ABO system. This system is based on the presence or absence of antigens A and/or B. These antigens are found on the surface of erythrocytes and on the surface of all endothelial and most epithelial cells as well. The major blood product used for transfusion is erythrocytes, which are red blood cells containing hemoglobin, the principal function of which is the transport of oxygen. Blood of group A contains antigen A on its erythrocytes. Similarly, blood of group B contains antigen B on its erythrocytes. Blood of group AB contains both antigens, and blood of group O contains neither antigen.

The blood group structures are glycoproteins or glycolipids and considerable work has been done to identify the specific structures making up the A and B determinants or antigens. It has been found that the blood group specificity is determined by the nature and linkage of monosaccharides at the ends of the carbohydrate chains. The carbohydrate chains are attached to a peptide or lipid backbone which is embedded in the lipid bi-layer of the membrane of the cells. The most important (immuno-dominant or immuno-determinant) sugar has been found to be N-acetylgalactosamine for the type A antigen and galactose for the type B antigen.

There are three recognized major sub-types of blood type A. These sub-types are known as $A_1$, A intermediate ($A_{int}$) and $A_2$. There are both quantitative and qualitative differences which distinguish these three sub-types. Quantitatively, $A_1$ erythrocytes have more antigenic A sites, i.e., terminal N-acetylgalactosamine residues, than $A_{int}$ erythrocytes which in turn have more antigenic A sites than $A_2$ erythrocytes. Qualitatively, the transferase enzymes responsible for the formation of A antigens differ biochemically from each other in $A_1$, A and $A_2$ individuals. Some A antigens found in $A_1$ cells contain dual A antigenic sites.

Blood of group A contains antibodies to antigen B. Conversely, blood of group B contains antibodies to antigen A. Blood of group AB has neither antibody, and blood group O has both. A person whose blood contains either (or both) of the anti-A or anti-B antibodies cannot receive a transfusion of blood containing the corresponding incompatible antigen(s). If a person receives a transfusion of blood of an incompatible group, the blood transfusion recipient's antibodies coat the red blood cells of the transfused incompatible group and cause the transfused red blood cells to agglutinate, or stick together. Transfusion reactions and/or hemolysis (the destruction of red blood cells) may result therefrom.

In order to avoid red blood cell agglutination, transfusion reactions and hemolysis, transfusion blood type is cross-matched against the blood type of the transfusion recipient. For example, a blood type A recipient can be safely transfused with type A blood which contains compatible antigens. Because type O blood contains no A or B antigens, it can be transfused into any recipient with any blood type, i.e., recipients with blood types A, B, AB or O. Thus, type O blood is considered "universal", and may be used for all transfusions. Hence, it is desirable for blood banks to maintain large quantities of type O blood. However, there is a paucity of blood type O donors. Therefore, it is useful to convert types A, B and AB blood to type O blood in order to maintain large quantities of universal blood products.

In an attempt to increase the supply of type O blood, methods have been developed for converting certain type A, B and AB blood to type O blood. For example, U.S. Pat. No. 4,609,627 entitled "Enzymatic Conversion of Certain Sub-Type A and AB Erythrocytes" ("the '627 Patent"), which is incorporated herein by reference, is directed to a process for converting $A_{int}$ and $A_2$ (including $A_2B$ erythrocytes) to erythrocytes of the H antigen type, as well as to compositions of type B erythrocytes which lack A antigens, which compositions, prior to treatment, contained both A and B antigens on the surface of said erythrocytes. The process for converting $A_{int}$ and $A_2$ erythrocytes to erythrocytes of the H antigen type which is described in the '627 Patent includes the steps of equilibrating certain sub-type A or AB erythrocytes, contacting the equilibrated erythrocytes with purified chicken liver α-N-acetylgalactosaminidase enzyme for a period sufficient to convert the A antigen to the H antigen, removing the enzyme from the erythrocytes and re-equilibrating the erythrocytes. As described in the '627

Patent, α-N-acetylgalactosaminidase obtained from an avian liver (specifically, chicken liver) source was found to have superior activity in respect of enzymatic conversion or cleavage of A antigenic sites.

Prior to the present invention, it was necessary to purify the enzyme from an avian liver source, a process which is time consuming and can be expensive. Hence, a need has arisen to develop an enzyme source which is more readily available. In addition, a need has arisen to develop an enzyme useful in blood product conversion which enzyme is cost-efficient.

A simplified purification process is described in a related application, Ser. No. 07/964,756, filed Oct. 22, 1992, entitled "Preparation of Enzyme for Conversion of Sub-Type A and AB Erythrocytes". This process, as described in the related application, utilizes chicken liver as a source of enzyme and, therefore, requires a number of purification steps. Despite this simplified process, it is still desirable to provide a more readily available and controlled source of enzyme, that being cloned and expressed enzyme. This would provide an enzyme source which is more consistent and which is readily purified at less cost and expense, with a still further reduced number of purification steps. Additionally, a recombinant, cloned enzyme allows for specific protein sequence modifications, which can be introduced to generate an enzyme with optimized specific activity, substrate specificity and pH range.

α-N-acetylgalactosaminidase enzymes are characterized (and thereby named) by their ability to cleave N-acetylgalactosamine sugar groups. In isolating or identifying these enzymes, their activity is assessed in the laboratory by evaluating cleavage of synthetic substrates which mimic the sugar groups cleaved by the enzymes, with p-nitrophenylglycopyranoside derivatives of the target sugar groups being commonly used. Although very useful in enzyme identification and isolation procedures (the quantitative cleavage of these synthetic substrates can be used to readily distinguish (and thereby identify) enzymes isolated from different sources), these synthetic substrates are simple structurally and small-sized and mimic only a portion of the natural glycoproteins and glycolipid structures which are of primary concern, those being the A antigens on the surface of cells.

A natural glycolipid substrate, originally isolated from sheep erythrocytes, is the Forsmann antigen (globopentaglycosylceramide). The Forsmann antigen substrate appropriately mimics the natural A antigen glycolipid structures and is therefore utilized to predict the activity of α-N-acetylgalactosaminidase enzymes against the A antigen substrate. Isolated Forsmann antigen glycolipids have been shown to inhibit hemolysis of sheep red cells by immune rabbit anti-A serum in the presence of serum complement.

α-N-acetylgalactosaminindase enzyme has been isolated from a number of sources besides chicken liver (described above), including bacteria, mollusks, earthworms, and human liver. The human α-N-acetylgalactosaminidase enzyme has been purified, sequenced, cloned and expressed. For example, in "Human α-N-Acetylgalactosaminidase—Molecular Cloning, Nucleotide Sequence and Expression of a Full-length cDNA", by Wang et al., in *The Journal of Biological Chemistry*, Vol. 265, No. 35, pages 21859–21866 (Dec. 15, 1990), the cDNA encoding human α-N-acetylgalactosaminidase was sequenced. In addition, in "Molecular Cloning of a Full-Length cDNA for Human α-N-Acetylgalactosaminidase (α-Galactosidase B)", by Tsuji et al., in *Biochemical And Biophysical Research Communications*, Vol. 163, No. 3, pages 1498–1504 (Sep. 29, 1989), the cDNA encoding human α-N-acetylgalactosaminidase was sequenced. Both the nucleotide sequence and the amino acid sequence of human α-N-acetylgalactosaminidase is published therein. Further, PCT Application No. WO 92/07936 discloses the cloning and expression of the cDNA which encodes human α-N-acetylgalactosaminidase.

Although human α-N-acetylgalactosaminidase has been purified, sequenced, cloned and expressed, it is not appropriate for use in removing A antigens from the surface of cells in blood products. In determining whether an enzyme is appropriate for use in removing A antigens from the surface of cells, one must consider the following enzyme characteristics, particularly with respect to the Forsmann antigen substrate: substrate specificity, specific activity or velocity of the substrate cleavage reaction, and pH optimum. Substrate specificity is measured in the Km value, which measures the binding constant or affinity of an enzyme for a particular substrate. The lower a Km value, the more tightly an enzyme binds its substrate. The velocity of an enzyme cleavage reaction is measured in the Vmax, the reaction rate at a saturating concentration of substrate. A higher Vmax indicates a faster cleavage rate. The ratio of these two parameters, Vmax/Km, is a measure of the overall efficiency of an enzyme in reacting with (cleaving) a given substrate. A higher Vmax/Km indicates greater enzyme efficiency. For successful and clinically applicable removal of A antigens from the surface of cells, the enzyme must be sufficiently active at or above a pH at which the cells being treated can be maintained. The procedure described in the '627 patent calls for treatment of cells at or above a pH of 5.6. Therefore, the pH optimum of an appropriate enzyme must still provide reasonable enzyme activity at this pH. These specific characteristics (Vmax/Km, Vmax, Km and pH optimum) are reported for the human α-N-acetylgalactosaminidase enzyme in "Studies on Human Liver α-galactosidases", by Dean et al. in *The Journal of Biological Chemistry*, Vol. 254, No. 20, pages 10001–10005 (1979).

The Vmax/Km value for the Forsmann antigen of human α-N-acetylgalactosaminidase is 0.46, as compared to a Vmax/Km value of 5.0 for the chicken liver enzyme, indicating an approximately ten-fold difference in efficiency. The Km is lower and the Vmax is higher for the chicken liver enzyme, compared to the human enzyme. Further, human α-N-acetylgalactosaminidase has a pH optimum for the Forsmann antigen of 3.9, compared to 4.7 for chicken liver α-N-acetylgalactosaminidase. By all of these enzyme characteristics, human α-N-acetylgalactosaminidase enzyme is not suitable for removal of A antigens, particularly when compared to the chicken liver enzyme.

As a result, a need still existed to develop an enzyme which is capable of removing A antigens from the surface of cells in blood products, wherein said enzyme is readily available and cost-efficient.

It is therefore an object of this invention to provide a recombinant enzyme for use in the removal of A antigens from the surface of cells in blood products.

It is another object of this invention to provide a recombinant enzyme for use in the removal of A antigens from the surface of cells in blood products wherein said enzyme is readily available and may be manufactured on a cost-efficient basis.

It is a further object of this invention to provide methods of cloning and expressing a recombinant enzyme useful in the removal of A antigens from the surface of cells in blood products.

It is yet another object of this invention to provide a method of removing A antigens from the surface of cells in blood products using a recombinant enzyme.

BRIEF DESCRIPTION OF THE DRAWINGS

The above brief description, as well as further objects and features of the present invention, will be more fully understood by reference to the following detailed description of the presently preferred, albeit illustrative, embodiment of the present invention when taken in conjunction with the accompanying drawing wherein:

FIGS. 2A and 2B represent the nucleic acid sequence and the deduced amino acid sequence of the chicken liver α-N-acetylgalactosaminidase cDNA clone;

FIG. 4 represents a homology comparison between α-N-acetylgalactosaminidases and α-galactosidases; and FIG. 5 represents the expression of chicken liver α-N-acetylgalactosaminidase in yeast as shown by Western blot.

SUMMARY OF THE INVENTION

Figure 1:
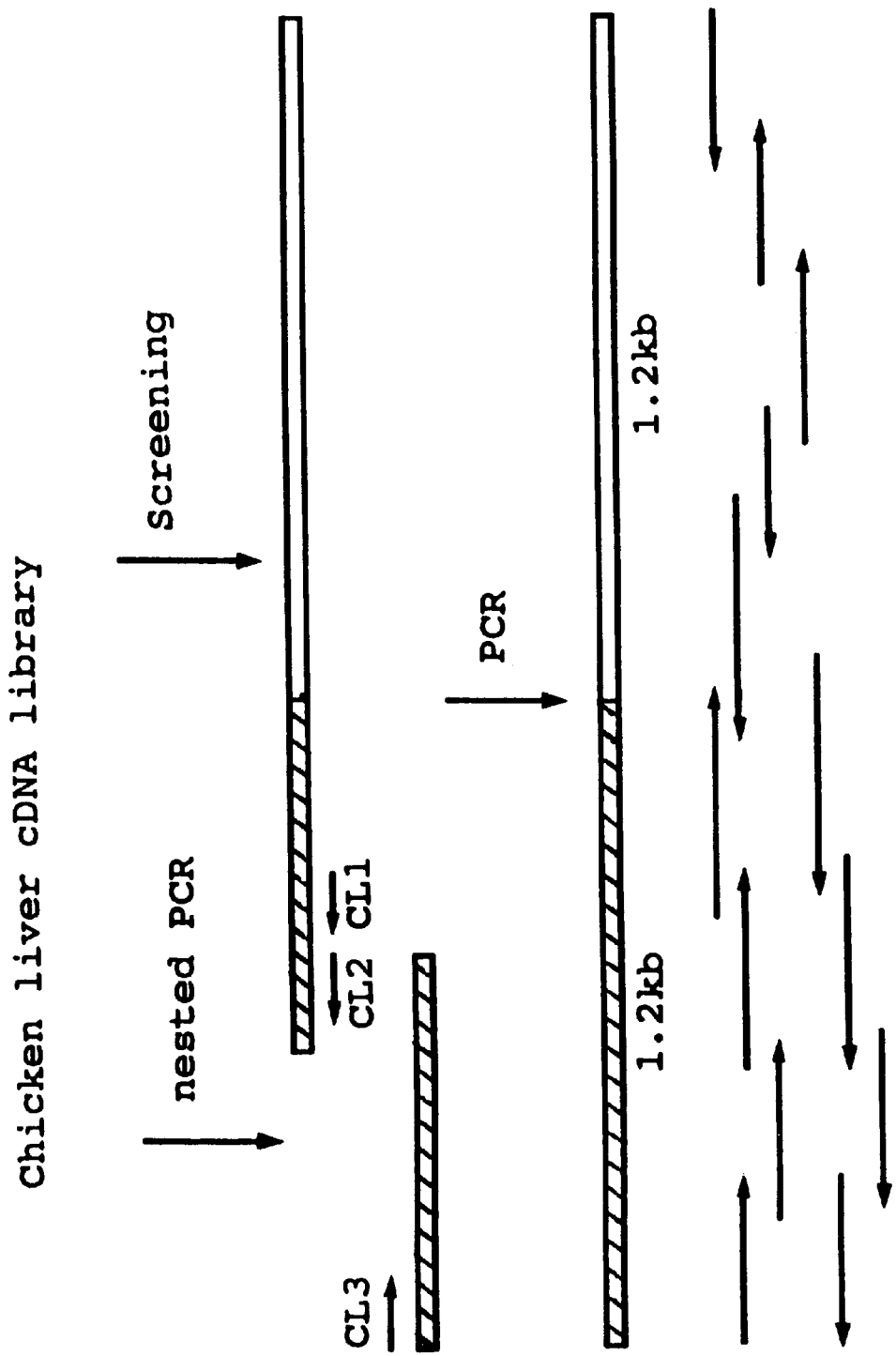
FIG. 1 represents a diagram of the strategy used to clone and sequence the chicken liver α-N-acetylgalactosaminidase cDNA.

This invention is directed to a recombinant chicken liver α-N-acetylgalactosaminidase enzyme, which enzyme has a molecular weight of about 45 kDa, is immunoreactive with an antibody specific for chicken liver α-N-acetylgalactosaminidase, and also has about 80% amino acid sequence homology with human α-N-acetylgalactosaminidase enzyme. The recombinant chicken liver α-N-acetylgalactosaminidase enzyme of this invention has the amino acid sequence depicted in FIG. 2, from amino acid number 1 to amino acid number 406. This invention is further directed to methods of cloning and expressing the recombinant chicken liver α-N-acetylgalactosaminidase enzyme, and to a method of using said enzyme to remove A antigens from the surface of cells in blood products so as to convert said blood products of certain A sub-types to type O, thereby rendering said blood products universal for use in transfusion therapy.

DETAILED DESCRIPTION OF THE INVENTION

This invention is directed to a recombinant enzyme for use in the removal of type A antigens from the surface of cells in blood products, thereby converting certain sub-type A blood products to type O blood products and certain sub-type AB blood products to type B blood products. The recombinant chicken liver α-N-acetylgalactosaminidase enzyme of this invention has a molecular weight of about 45 kDa and is immunoreactive with an antibody specific for chicken liver α-N-acetylgalactosaminidase. In addition, the recombinant enzyme of this invention has about 80% amino acid sequence homology with human α-N-acetylgalactosaminidase enzyme. The recombinant chicken liver α-N-acetylgalactosaminidase enzyme of this invention has the following nucleic acid and deduced amino acid sequence:

```
                                                         SEQ ID NO 1:
ATG CTG GAG AAC GGG CTG GCG CGG ACC CCG CCC ATG GGC TGG TTG GCC
Met Leu Glu Asn Gly Leu Ala Arg Thr Pro Pro Met Gly Trp Leu Ala

TGG GAG CGG TTC CGC TGC AAC GTG AAC TGC CGG GAG GAC CCC CGC CAG
Trp Glu Arg Phe Arg Cys Asn Val Asn Cys Arg Glu Asp Pro Arg Gln

TGC ATC AGT GAG ATG CTC TTC ATG GAG ATG GCA GAC CGA ATA GCA GAG
Cys Ile Ser Glu Met Leu Phe Met Glu Met Ala Asp Arg Ile Ala Glu

GAC GGC TGG AGG GAG CTG GGC TAC AAG TAC ATC AAT ATC GAT GAC TGC
Asp Gly Trp Arg Glu Leu Gly Tyr Lys Tyr Ile Asn Ile Asp Asp Cys

TGG GCC GCC AAG CAG CGT GAC ACT GAG GGG CGG CTG GTG CCT GAC CCC
Trp Ala Ala Lys Gln Arg Asp Thr Glu Gly Arg Leu Val Pro Asp Pro

GAG AGG TTC CCC CGG GGC ATT AAG GCC TTG GCT GAC TAC GTT CAT GCC
Glu Arg Phe Pro Arg Gly Ile Lys Ala Leu Ala Asp Tyr Val His Ala

CGA GGC TTG AAG CTG GGC ATT TAT GGC GAC CTG GGC AGA CTC ACC TGT
Arg Gly Leu Lys Leu Gly Ile Tyr Gly Asp Leu Gly Arg Leu Thr Cys

GGA GGC TAC CCA GGC ACC ACG CTG GAC CGT GTG GAG CAG GAC GCA CAG
Gly Gly Tyr Pro Gly Thr Thr Leu Asp Arg Val Glu Gln Asp Ala Gln

ACC TTC GCT GAG TGG GGT GTG GAC ATG CTG AAG CTA GAT GGG TGC TAC
Thr Phe Ala Glu Trp Gly Val Asp Met Leu Lys Leu Asp Gly Cys Tyr

TCA TCG GGG AAG GAG CAG GCA CAG GGC TAC CCA CAA ATG GCA AGG GCC
Ser Ser Gly Lys Glu Gln Ala Gln Gly Tyr Pro Gln Met Ala Arg Ala

TTG AAC GCC ACT GGC CGC CCC ATC GTC TAC TCC TGC AGC TGG CCA GCC
Leu Asn Ala Thr Gly Arg Pro Ile Val Tyr Ser Cys Ser Trp Pro Ala

TAC CAG GGG GGG CTG CCT CCC AAG GTG AAC TAC ACT CTC CTG GGT GAG
Tyr Gln Gly Gly Leu Pro Pro Lys Val Asn Tyr Thr Leu Leu Gly Glu

ATC TGC AAC CTG TGG CGG AAC TAC GAT GAC ATC CAG GAC TCA TGG GAC
Ile Cys Asn Leu Trp Arg Asn Tyr Asp Asp Ile Gln Asp Ser Trp Asp
```

-continued

```
AGC GTG CTT TCC ATC GTG GAC TGG TTC TTC ACA AAC CAG GAT GTG CTG
Ser Val Leu Ser Ile Val Asp Trp Phe Phe Thr Asn Gln Asp Val Leu

CAG CCG TTT GCT GGC CCT GGC CAC TGG AAT GAC CCA GAC ATG CTC ATC
Gln Pro Phe Ala Gly Pro Gly His Trp Asn Asp Pro Asp Met Leu Ile

ATT GGA AAT TTC GGT CTC AGC TAT GAG CAG TCA CGT TCC CAA ATG GCC
Ile Gly Asn Phe Gly Leu Ser Tyr Glu Gln Ser Arg Ser Gln Met Ala

TTG TGG ACC ATT ATG GCA GCT CCA CTC CTC ATG TCC ACC GAC CTG CGC
Leu Trp Thr Ile Met Ala Ala Pro Leu Leu Met Ser Thr Asp Leu Arg

ACT ATC TCG CCG AGT GCC AAG AAG ATT CTG CAG AAC CGC CTG ATG ATC
Thr Ile Ser Pro Ser Ala Lys Lys Ile Leu Gln Asn Arg Leu Met Ile

CAG ATA AAC CAG GAC CCC TTG GGA ATC CAG GGG CGC AGG ATC ATC AAG
Gln Ile Asn Gln Asp Pro Leu Gly Ile Gln Gly Arg Arg Ile Ile Lys

GAG GGA TCC CAC ATT GAG GTG TTC CTG CGC CCG CTG TCA CAG GCT GCC
Glu Gly Ser His Ile Glu Val Phe Leu Arg Pro Leu Ser Gln Ala Ala

AGT GCC CTG GTC TTC TTC AGC CGG AGG ACA GAC ATG CCC TTC CGC TAC
Ser Ala Leu Val Phe Phe Ser Arg Arg Thr Asp Met Pro Phe Arg Tyr

ACC ACC AGT CTT GCC AAG CTT GGC TTC CCC ATG GGA GCT GCA TAT GAG
Thr Thr Ser Leu Ala Lys Leu Gly Phe Pro Met Gly Ala Ala Tyr Glu

GTG CAA GAC GTG TAC AGT GGG AAG ATC ATC AGT GGC CTG AAG ACA GGA
Val Gln Asp Val Tyr Ser Gly Lys Ile Ile Ser Gly Leu Lys Thr Gly

GAC AAC TTC ACA GTG ATC ATC AAC CCC TCA GGG GTG GTG ATG TGG TAC
Asp Asn Phe Thr Val Ile Ile Asn Pro Ser Gly Val Val Met Trp Tyr

CTG TGT CCC AAA GCA CTG CTC ATC CAG CAG CAA GCT CCT GGG GGG CCC
Leu Cys Pro Lys Ala Leu Leu Ile Gln Gln Gln Ala Pro Gly Gly Pro

TCG CGC CTG CCC CTT CTG TGA GGC CCA TGA TTG GGA GCC CTG GGA TAC
Ser Arg Leu Pro Leu Leu ***

ATC TCA CCG CTG CTC AAG TGC CTT CTT CTG GTG TGG CTG GGG GAG GAC

ATG CAG CTT GCT CCT CTG GCA CCA CCT GAT GAT TTC TAC TCA TTC CAC

GTG AAG CAG GAC TTC TTG TTA CTC CCT CCT GAG AGC ATG CAA AGC GCT

CTG AGG TCC TCC TGT GGA AGA GGA GTG TTC CCA GTG ACC ATC CTT TAG

GAC CAG ATG TGG TCA CCT TTT TTC CTT TGC TTG GCT TAG GAC AAA GGG

CTG TCC ACA GGC TGC ACC CCT CTT CCC AGG CAC CAT CCC CAG ACC AGG

AGC TCC TGG GGC CAG GCT GTC TCT GTC TGG CAG CAG GAT CAG CAG GTA

ACA CCA CTA CAG TGT AGT CCG CAC ATA ATG AAA AAG AAA TCT AAA CAA

AAC GTG TGC CAG TAG TGT ACT GAA CCC GCT CTG GTT ACA GCA GAG CAA

AAC CTG AGT TGT CCA TGC ACA ATC CCA GTA TCC TCA CTG TGG TGT TAG

CAT GAA AAA TTG CAG TCA CAG TGC ATT GTG CAC GAG TGG TGT CTG GAA

GAT GCT GAT GCT TGT TCG TGG TGG TCT TAA GGT GGG AGA TGC TCA TGG

GTG CTG GCC AAG TTG CAT CTC AAT CTT GTG AGG CTG AAC CTT CCA GCA

TTT CTC AGG GAA AGG CTC TTC CTT TTA AAG GCA GCC TGC ACA AAT AGA

AGG GGC TCA GAA GGA CGC ACG AGG AGG GGC TCA GGT GGG CCG TGC TCC

CCT GAC CAC CCC AAG AGG GGT CAA CTA CTC ACC AAA ATC TAC CCC TTT

CAA GGC CAG GTC AGC CCA GGG AGA CGC ACC CAA GGT TAA ACC TCA AAA

CAG GAA ATC ACC CTA TTT TAA ATT AGT GAG AAA TTG AAC TTC CCC ATT

CTA TTC AGA TGA GGG CTA GAA GCC CAC TCT CCT TAG AAG GCA CGT GGT

GGA TTC CTG CCC CTT GCA GAG ACA TTG TGG TCT GAA GCA AGA TGC TGA
```

```
-continued
ATG TGA TCT TTG CAG CGC TGG AAA TGA CAT GTC TGT TTC ATG CTT GTG

TGG GAG ATG GCT TTG TTT TTG TGA TTT TGA CAA TTT AAC TGA AAT AAA

AGG GAA GCA GAG GGG
```

A DNA vector containing a sequence encoding chicken liver α-N-acetylgalactosamindase was deposited under the Budapest Treaty with the American Type Culture Collection, Rockville, Md. on Mar. 17, 1993, tested and found viable on Mar. 22, 1993 and catalogued as ATCC No. 7534.

The recombinate chicken liver α-N-acetylglactosaminidase enzyme of this invention can be cloned and expressed so that it is readily available for use in the removal of A antigens from the surface of cells in blood products. The enzyme of this invention can be cloned and expressed by screening chicken liver cDNA library to obtain the cDNA sequence which encodes the chicken liver α-N-acetylgalactosaminidase, sequencing the encoding cDNA once it is determined, cloning the encoding cDNA and expressing α-N-acetylgalactosaminidase from the cloned encoding cDNA. This may be performed by obtaining an amplified human α-N-acetylgalactosaminidase fragment capable of use as a screening probe, screening a chicken liver cDNA library, such as the one described hereinabove, using the amplified human α-N-acetylgalactosaminidase fragment as a probe so as to obtain the cDNA sequence of the chicken liver cDNA library which encodes chicken liver α-N-acetylgalactosaminidase, sequencing the encoding DNA, cloning the encoding DNA and expressing chicken liver α-N-acetylgalactosaminidase enzyme from the cloned encoding cDNA. Alternatively, screening can be performed using antibodies which recognize chicken liver α-N-acetylgalactosaminidase.

Methods which are well known to those skilled in the art can be used to construct expression vectors containing the chicken liver α-N-acetylgalactosaminidase coding sequence, with appropriate transcriptional/translational signals for expression of the enzyme in the corresponding expression systems. Appropriate organisms, cell types and expression systems include: cell-free systems such as a rabbit reticulocyte lysate system, prokaryotic bacteria, such as *E. coli,* eukaryotic cells, such as yeast, insect cells, mammalian cells (including human hepatocytes or Chinese hamster ovary (CHO) cells), plant cells or systems, and animal systems including oocytes and transgenic animals.

The entire chicken liver α-N-acetylgalactosaminidase coding sequence or functional fragments of functional equivalents thereof may be used to construct the above expression vectors for production of functionally active enzyme in the corresponding expression system. Due to the degeneracy of the DNA code, it is anticipated that other DNA sequences which encode substantially the same amino acid sequence may be used. Additionally, changes to the DNA coding sequence which alter the amino acid sequence of the chicken liver α-N-acetylgalactosaminidase enzyme may be introduced which result in the expression of functionally active enzyme. In particular, amino acid substitutions may be introduced which are based on similarity to the replaced amino acids, particularly with regard to the charge, polarity, hydrophobicity, hydrophilicity, and size of the side chains of the amino acids.

Once a recombinant chicken liver α-N-acetylgalactosaminidase enzyme is cloned and expressed, said enzyme can be used to remove A antigens from the surface of cells in blood products. Methods of utilizing chicken liver α-N-acetylgalactosaminidase to remove A antigens from the surface of erythrocytes can be found in U.S. Pat. No. 4,609,627 issued Sep. 2, 1986 to Goldstein, entitled "Enzymatic Conversion of Certain Sub-type A and AB Erythrocytes", which is incorporated herein by reference. Sub-type A antigens can be removed from the surface of erythrocytes by contacting the erythrocytes with the recombinant chicken liver α-N-acetylgalactosaminidase enzyme of this invention for a period of time sufficient to remove the A antigens from the surface of the erythrocytes.

EXAMPLE

Isolation and Characterization of the Chicken Liver cDNA Clone

Chicken liver α-N-acetylgalactosaminidase was purified to homogeneity. The enzyme was a glycoprotein with a molecular weight of 80 kDa, and was dissociated into two identical subunits at pH 7.5. Its optimal pH for cleavage of the synthetic p-nitrophenyl-α-N-acetylgalactosaminylpyranoside substrate was 3.65 and the activity dropped sharply when the pH was raised above 7. The N-terminal sequence obtained from the purified chicken liver α-N-acetylgalactosaminidase showed a strong homology with the corresponding sequence deduced from the human α-N-acetylgalactosaminidase cDNA clone described in Tsuji et al., and Wang et al.

In order to isolate and characterize the cDNA clone for chicken liver α-N-acetylgalactosaminidase, two oligonucleotides, corresponding to nucleotides 688 to 705 and 1219 to 1236 of the human α-N-acetylgalactosaminidase sequence published by Wang, et al. were synthesized. Using human placental mRNA (Clontech) as a template, the specific cDNA was made from the downstream (C-terminal) oligonucleotide. Next, a DNA fragment corresponding to human α-N-acetylgalactosaminidase residues from 688 to 1236 was amplified from the cDNA by the hot-start PCR technique. The PCR reaction mixture was preheated at 95° C. for 5 minutes and maintained at 80° C. while Taq DNA polymerase (Promega) was added to reduce the possible non-specific annealing at lower temperature. 35 cycles of amplification was then carried out as follows: 94° C. for 1 minute, 50° C. for 2 minutes and 72° C. for 3 minutes. The same conditions for PCR were applied in all of the following experiments.

The PCR-amplified fragment was then used as a radioactively-labeled probe in the screening of a chicken liver cDNA library (Stratagene) based on homology hybridization. The filters containing the library were hybridized with the probe overnight at 42° C. in a solution of 50% formamide, 5×SSPE, 5×Denhardt's, 0.1% SDS and 0.1 mg/ml salmon sperm DNA. The filters were then washed as follows:

1. 3×SSC+0.1% SDS, 20 min. room temperature
2. 2×SSC+0.1% SDS, 20 min. room temperature
3. 1×SSC+0.1% SDS, 20 min. 56° C.
4. 1×SSC+0.1% SDS, 20 min. 56° C.

The filters were autoradiographed overnight at −70° C. The positive clones were picked up for the second-round screening following the same procedure. In total, three consecutive screenings were carried out in order to obtain a well-isolated positive clone.

From approximately one million plaques screened, one positive clone was successfully isolated. The sequencing data indicated that the clone consists of a 1.2 kb 3'-untranslated region and a 0.7 kb coding region which is highly homologous to human α-N-acetylgalactosaminidase. In order to obtain the missing coding sequence, the library was rescreened by using the 1.9 kb cDNA clone as a probe. However, no positive clone was identified by this approach.

The upstream cDNA sequence was then obtained by applying multiple amplification (the nested PCR technique) of a second chicken liver cDNA library (Clontech). FIG. 1 represents a diagram of the strategy used to clone and sequence the chicken liver α-N-acetylgalactosaminidase cDNA. The cDNA encoding chicken liver α-N-acetylgalactosaminidase contained a 1.2 kb coding region (slashed area) and a 1.2 kb 3' untranslated region. The arrows at the bottom of the diagram indicate the sequencing strategy. CL1, CL2 and CL3 are oligonucleotides used as primers for the nested PCR. CL1 and CL2 are located at position 924–941 nt and 736–753 nt, respectively (see FIG. 2). According to the N-terminal sequence of native chicken liver enzyme, the oligonucleotide CL3 [5'-CTGGAGAAC(T)GGA(GC)CTGGCT(CA)CG] was designed taking into account chicken codon usage and "best guess".

In the first-round PCR amplification, the whole cDNA library was used as a template in the presence of one specific primer (CL1) (see FIG. 1) and one universal primer derived from the library vector (5'-CTGGTAATGGTAGCGACC). A small aliquot from the above reaction was directly taken for the second-round amplification with a different set of primers. The primer CL2 had the sequence located upstream of CL1 (FIG. 1) and the second primer, CL3, was designed based on the N-terminal amino acid sequence -from purified chicken liver α-N-acetylgalactosaminidase (see FIG. 1). A 750 bp fragment was sequenced to eliminate any possible PCR artifacts. Since the 750 bp fragment overlapped with the 1.9 kb clone isolated by the library-screening, the two fragments were linked together by PCR to reconstitute the cDNA encoding chicken liver α-N-acetylgalactosaminidase (FIG. 1). The DNA sequencing was performed according to standard procedure, and the coding region was sequenced in both orientations.

The Cloned DNA Encodes Chicken Liver α-N-Acetylgalactosaminidase

The authenticity of the cDNA clone was established by co-linearity of deduced amino acid sequences with N-terminal and CNBr-digested peptide sequences from purified chicken liver α-N-acetylgalactosaminidase. FIG. 2 represents the nucleic acid sequence and deduced amino acid sequence of the chicken liver α-N-acetylgalactosaminidase cDNA clone. The underlined regions in FIG. 2 match sequences obtained from the N-terminus and CNBr-derived fragments of enzyme purified from chicken liver. The first 3 nucleotides, ATG, were added during subcloning to serve as the translational initiation codon for protein expression. The polyadenylation signal (AATAAA) at positions 2299–2304 nt is double-underlined. The boxed sequence indicates potential sites for N-glycosylation. According to the cDNA, the mature protein of 405 amino acids has a molecular mass of about 45 kDa, consistent with that of the purified enzyme estimated by SDS-PAGE. Due to the cloning approach applied, the sequence at the 5' end of the cDNA corresponded to the N-terminal sequence of the mature enzyme isolated from chicken liver.

In order to express the chicken liver α-N-acetylgalactosaminidase in a rabbit reticulocyte lysate, the sequence from 1 to 1260 nucleotides which contained the coding region for chicken liver α-N-acetylgalactosaminidase was subcloned into the vector PCR-II (Invitrogen) in such an orientation that the T7 promoter was located upstream of the insert. Since the N-terminus of the mature protein started with leucine, a translational initiation codon, ATG, was added during the subcloning construction. The construct was then used as a template in a transcription-translation coupled system, TNT system (Promega), for protein expression according to the procedure recommended by the manufacturer.

In order to produce the recombinant α-N-acetylgalactosaminidase in large quantities in bacteria and purify the enzyme in a single-step fashion, the cDNA was subcloned into the EcoRI site of the pTrcHis vector (Invitrogen) for expression in E. coli. Because of the sequence in the vector, the expressed enzyme contained a polyhistidine-tag in its N-terminus, which permitted one step purification by affinity chromatography from crude cell lysates.

Figure 3:
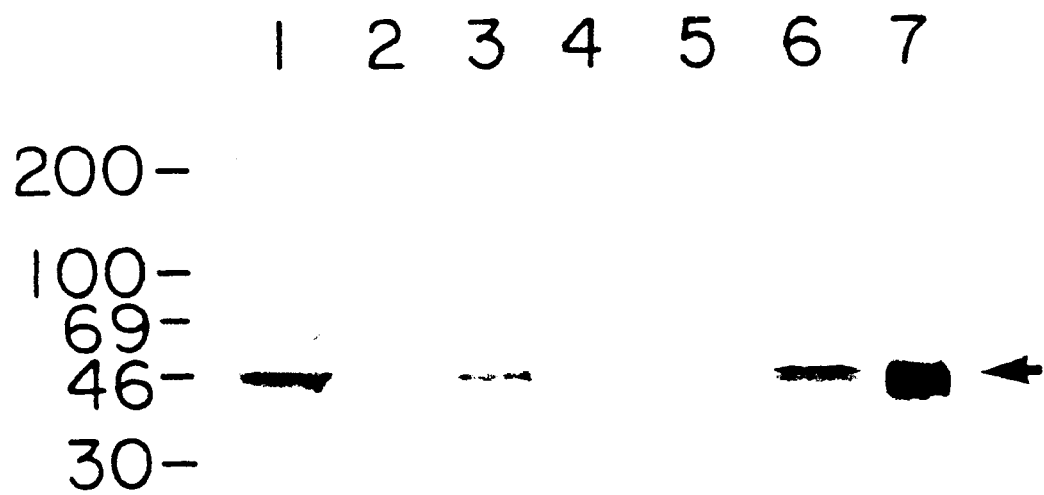
FIG. 3 represents the expression of chicken liver α-N-acetylgalactosaminidase in bacteria and rabbit reticulocyte lysate as shown by Western blot.

FIG. 3 represents the expression of chicken liver α-N-acetylgalactosaminidase in bacteria and rabbit reticulocyte lysate as shown by Western blotting. Lane 1 through lane 4 demonstrate the results of expression in a rabbit reticulocyte lysate. The expression was carried out in lysate in the presence of $^{35}$S-methionine with (lane 1) or without (lane 2) the expression plasmid. Next, 5 μl of the reaction sample was loaded to a 12% SDS-PAGE. The gel was dried and autoradiographed for 2 hours and a band of an apparent molecular weight of about 45 KDa was visualized with the expression plasmid (lane 1, FIG. 3). In order to confirm the authenticity of the expressed protein, a Western blot was performed using a polyclonal antibody raised against α-N-acetylgalactosaminidase purified from chicken liver. Using non-labelled methionine instead, the same expression reaction was performed for a Western blot (Promega) as shown in lanes 3 and 4, with and without the expression plasmid, respectively. As indicated in FIG. 3, the antibody specifically recognized a band from the reaction with expression plasmid (lane 3), but not in the control (lane 4). Lane 5 shows the protein expressed in bacteria and recognized by the same antibody on Western blot. Lane 6 shows the α-N-acetylgalactosaminidase purified from chicken liver as a positive control. Molecular weight size marker (m) is indicated on the left. Hence, it was confirmed that the isolated cDNA clone codes for the chicken liver α-N-acetylgalactosaminidase.

Comparison of the Cloned Chicken Liver Sequence with other Enzyme Sequences

The chicken liver α-N-acetylgalactosaminidase sequence was compared with published sequences of other α-N-acetylgalactosaminidases and α-galactosidases which cleave α-galactose sugar groups. FIG. 4 shows a homology comparison between various α-N-acetylgalactosaminidases and α-galactosidases. Alignment was carried out using both the computer program PROSIS (Hitachi Software Engineering Corp., Ltd.) and manual arrangement. The amino acid sequences were deduced from cDNAs. Sequences I and II are of α-N-acetylgalactosaminidases from chicken liver and human placenta, respectively. Sequences III, IV, V and VI represent α-galactosidase from human, yeast, *Cyamopsis tetragonoloba* and *Aspergillus niger*, respectively. Sequences IV and VI are truncated at the C-terminus, as indicated by **. Identical or conservatively substituted amino acid residues (five out of six or more) among the aligned protein sequences are boxed. The numbers above the sequences indicate the relative position of each peptide sequence.

The deduced amino acid sequence from chicken liver α-N-acetylgalactosaminidase cDNA shows approximately 80% homology with the human α-N-acetylgalactosaminidase as determined by PROSIS. This homology indicates the relatedness of the human and chicken liver enzymes, despite the differences in the specific characteristics of the enzymes, particularly with regard to cleavage of the Forsmann antigen, as has already been described. Also, polyclonal antibodies raised against chicken liver α-N-acetylgalactosaminidase enzyme do not cross react with the human enzyme. The specific amino acids responsible for these differences remain to be elucidated.

Yamachi et al. (1990) reported that a human α-N-acetylgalactosaminidase cDNA with an insertion of 70 bp at the position corresponding to number 376 in FIG. 4 was not enzymatically active in a transient expression study in COS cells. The data suggests that the open reading frame shift caused by this insertion in the C-terminal portion of the molecule is responsible for the loss of enzymatic activity, indicating that amino acids in the C-terminal region may be essential for α-N-acetylgalactosaminidase enzyme activity.

By sequence similarity searching (BLAST) (Altschul et al. 1990) of available protein databases followed by sequence alignment using the PROSIS computer program and manual arrangement, it was found that α-N-acetylgalactosaminidase is highly homologous to α-galactosidases from human, yeast, cyamopsis tetragonoloba and aspergillus niger (ranging from 55% to 68% at the amino acid level). The extent of the amino acid sequence homology, as shown in FIG. 4, suggests that these two functionally specific glycosidases might have evolved from a common ancestral gene. Considering the high degree of similarities and the nature of their substrates it is possible that the two exoglycosidases share a similar catalytic mechanism and the critical amino acid residues involved in both active sites are well conserved. The addition of chicken liver α-N-acetylgalactosaminidase cDNA to the family provides further insight into regions of the molecule which are important for the substrate binding specificity and enzymatic activity. Given the availability of cloned enzymes from a number of sources, the active site and catalytic mechanisms of α-N-acetylgalactosaminidase and α-galactosidase enzymes may now be studied by means of cDNA deletion and site-directed mutagenesis.

Expression of Active Chicken Liver α-N-acetylgalactosaminidase in Yeast

The first 48 nucleotides of human α-N-acetylgalactosaminidase cDNA (Wang, et al. 1990) which correspond to the signal peptide sequence, were linked to the cloned chicken liver α-N-acetylgalactosaminidase coding region by PCR. The PCR amplified product was subcloned directly into the vector PCR-II (Invitrogen). Two EcoR1 sites flanking the insert were used to subclone the entire α-N-acetylgalactosaminidase cDNA into the yeast expression vector pYES2 (Invitrogen) in such an orientation that the GAL 1 promoter was located upstream of the insert. The GAL 1 promoter provides expression of the inserted cDNA clone under galactose inducing growth conditions in yeast.

The yeast vector constructs were transformed into the yeast strain, INVSCI (Invitrogen) using standard procedures. To confirm the expression of the chicken liver α-N-acetylgalactosaminidase in yeast, the total proteins from cell extract and culture supernatant were prepared and separated by 12% SDS-PAGE and a Western blot performed (by standard conditions) using the polyclonal antibody raised against purified chicken liver α-N-acetylgalactosaminidase. The transformed yeast cells were grown in medium without uracil (Bio 101, Inc.). After 0.2% galactose induction, the cells were centrifuged and protein extracts were prepared using glass bead disruption. The secreted proteins in the culture supernatant were concentrated with a Centricon-30 (Amicon Division, W. R. Grace & Co.). The Western blot results are depicted in FIG. 5.

Figure 5:
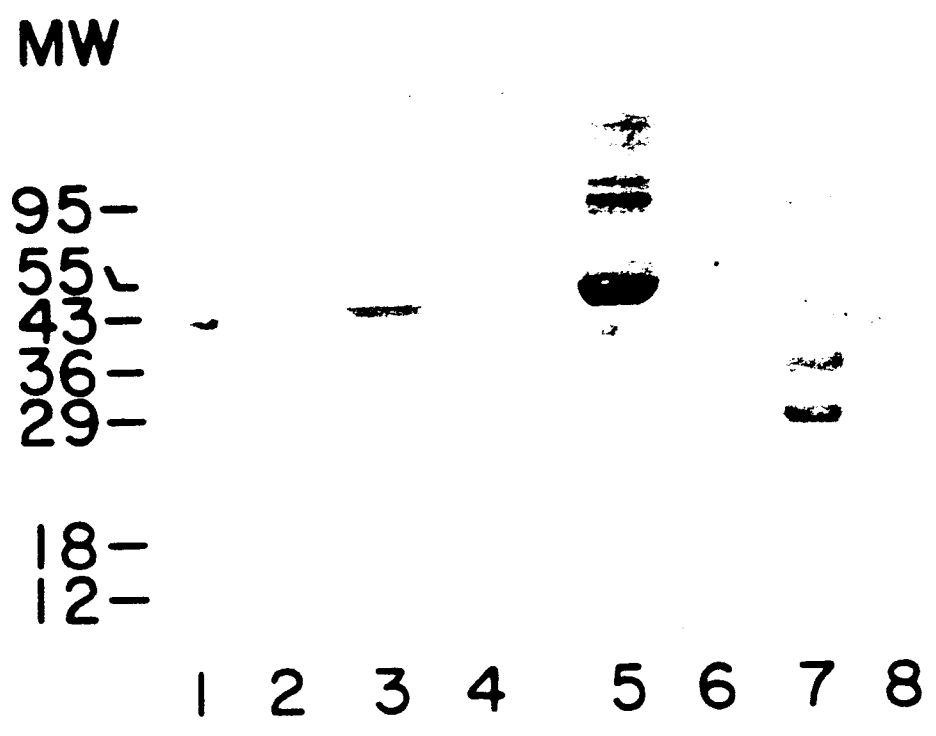

Lanes 1 and 8 of FIG. 5 show the α-N-acetylgalactosaminidase purified from chicken liver. Lane 2 through lane 4 are cell extracts from the yeast transformed with three different pYES2 constructs: the vector alone (lane 2), chicken liver α-N-acetylgalactosaminidase cDNA coding region (lane 3), and the coding region plus signal sequence (lane 4). Lane 5 is the culture supernatant from yeast used in Lane 4. Lane 7 shows the molecular weight standard. As shown in FIG. 5, while the protein without signal peptide was expressed within yeast cells (lane 3), the protein with a signal peptide sequence was predominantly secreted into the media (lane 5). The larger molecular weight of the secreted protein observed on the Western blot was presumably caused by overglycosylation, as was observed for the expression of guar α-galactosidase in yeast (Fellinger, et al. 1991).

To purify the expressed α-N-acetylgalactosaminidase, concentrated culture supernatant was applied to an affinity column containing aminocaproylgalactosylamine agarose. After washing the column, the bound fraction was eluted with buffer containing 50 mM N-acetylgalactosamine. This eluate contains expressed α-N-acetylgalactosaminidase of similar molecular weight to that of the enzyme purified from chicken liver, as indicated in lane 6 in FIG. 5.

The expressed enzyme eluted from the column demonstrates activity toward the synthetic substrate p-nitrophenyl-α-N-acetylgalactosaminylpyranoside at pH 3.6. Heavily glycosylated enzyme did not bind to the affinity column and showed no activity against synthetic substrate. All the data taken together demonstrate production, secretion and purification of enzymatically active chicken liver α-N-acetylgalactosaminidase in yeast cells.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claim is:

1. An isolated nucleic acid molecule selected from the group consisting of:
   (a) nucleic acid molecules which hybridize under stringent conditions to a nucleic acid molecule sequence set forth as SEQ ID NO:1, and which code for a chicken liver α-N-acetylgalactosaminidase enzyme, wherein the stringent conditions comprise hybridization at 42° C. in a solution of 50% formamide, 5X SSPE, 5X Denhardt's, 0.1% SDS and 0.1 mg/ml salmon sperm DNA, and
   (b) complements of (a).

2. An isolated nucleic acid molecule comprising a nucleotide sequence encoding the amino acid sequence set forth as SEQ ID NO:2.

3. The isolated nucleic acid molecule of claim 2 comprising the nucleotide sequence set forth as SEQ ID NO:1.

4. A vector comprising a nucleic acid molecule encoding the amino acid sequence set forth as SEQ ID NO:2.

5. The vector of claim 4, wherein the nucleic acid molecule comprises the nucleotide sequence set forth as SEQ ID NO:1.

6. The vector of claim 4, wherein the nucleic acid molecule is operably linked to a promoter.

7. A cell transformed with the vector of claim 4.

8. A cell transformed with the vector of claim 5.

9. A method for producing recombinant chicken liver α-N-acetylgalactosaminidase enzyme, comprising culturing the cell of claim 7, and recovering chicken liver α-N-acetylgalactosaminidase enzyme from the culture.

10. A method for producing recombinant chicken liver α-N-acetylgalactosaminidase enzyme, comprising culturing the cell of claim 8, and recovering chicken liver α-N-acetylgalactosaminidase enzyme from the culture.

* * * * *

SEQUENCE LISTING (1) GENERAL INFORMATION:

(iii) NUMBER OF SEQUENCES:  7

(2) INFORMATION FOR SEQ ID NO:  1:

(i) SEQUENCE CHARACTERISTICS:
        (A) LENGTH:  2319
        (B) TYPE:    nucleic acid
        (C) STRANDEDNESS:  double
        (D) TOPOLOGY:   linear (ii) MOLECULE TYPE:
        (A) DESCRIPTION:  cDNA to mRNA (iii) HYPOTHETICAL:    no (iv) ANTI-SENSE:      yes (v) FRAGMENT TYPE:

(vi) ORIGINAL SOURCE:
        (A) ORGANISM:   chicken liver
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:    library (viii) POSITION IN GENOME:  unknown
        (A) CHROMOSOME/SEGMENT:
        (B) MAP POSITION:
        (C) UNITS:

(ix) FEATURE:
        (A) NAME/KEY:    chicken liver a-N-acetylgalactosaminidase
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:  1:

```
ATG CTG GAG AAC GGG CTG GCG CGG ACC CCG CCC ATG GGC TGG TTG GCC       48
Met Leu Glu Asn Gly Leu Ala Arg Thr Pro Pro Met Gly Trp Leu Ala
 1               5                  10                  15

TGG GAG CGG TTC CGC TGC AAC GTG AAC TGC CGG GAG GAC CCC CGC CAG       96
Trp Glu Arg Phe Arg Cys Asn Val Asn Cys Arg Glu Asp Pro Arg Gln
                20                  25                  30

TGC ATC AGT GAG ATG CTC TTC ATG GAG ATG GCA GAC CGA ATA GCA GAG      144
Cys Ile Ser Glu Met Leu Phe Met Glu Met Ala Asp Arg Ile Ala Glu
         35                  40                  45

GAC GGC TGG AGG GAG CTG GGC TAC AAG TAC ATC AAT ATC GAT GAC TGC      192
Asp Gly Trp Arg Glu Leu Gly Tyr Lys Tyr Ile Asn Ile Asp Asp Cys
 50                  55                  60
```

```
                                                        -continued

TGG GCC GCC AAG CAG CGT GAC ACT GAG GGG CGG CTG GTG CCT GAC CCC          240
Trp Ala Ala Lys Gln Arg Asp Thr Glu Gly Arg Leu Val Pro Asp Pro
 65                  70                  75                  80

GAG AGG TTC CCC CGG GGC ATT AAG GCC TTG GCT GAC TAC GTT CAT GCC          288
Glu Arg Phe Pro Arg Gly Ile Lys Ala Leu Ala Asp Tyr Val His Ala
                 85                  90                  95

CGA GGC TTG AAG CTG GGC ATT TAT GGC GAC CTG GGC AGA CTC ACC TGT         336
Arg Gly Leu Lys Leu Gly Ile Tyr Gly Asp Leu Gly Arg Leu Thr Cys
            100                 105                 110

GGA GGC TAC CCA GGC ACC ACG CTG GAC CGT GTG GAG CAG GAC GCA CAG         384
Gly Gly Tyr Pro Gly Thr Thr Leu Asp Arg Val Glu Gln Asp Ala Gln
        115                 120                 125

ACC TTC GCT GAG TGG GGT GTG GAC ATG CTG AAG CTA GAT GGG TGC TAC         432
Thr Phe Ala Glu Trp Gly Val Asp Met Leu Lys Leu Asp Gly Cys Tyr
130                 135                 140

TCA TCG GGG AAG GAG CAG GCA CAG GGC TAC CCA CAA ATG GCA AGG GCC         480
Ser Ser Gly Lys Glu Gln Ala Gln Gly Tyr Pro Gln Met Ala Arg Ala
145                 150                 155                 160

TTG AAC GCC ACT GGC CGC CCC ATC GTC TAC TCC TGC AGC TGG CCA GCC         528
Leu Asn Ala Thr Gly Arg Pro Ile Val Tyr Ser Cys Ser Trp Pro Ala
                165                 170                 175

TAC CAG GGG GGG CTG CCT CCC AAG GTG AAC TAC ACT CTC CTG GGT GAG         576
Tyr Gln Gly Gly Leu Pro Pro Lys Val Asn Tyr Thr Leu Leu Gly Glu
            180                 185                 190

ATC TGC AAC CTG TGG CGG AAC TAC GAT GAC ATC CAG GAC TCA TGG GAC         624
Ile Cys Asn Leu Trp Arg Asn Tyr Asp Asp Ile Gln Asp Ser Trp Asp
        195                 200                 205

AGC GTG CTT TCC ATC GTG GAC TGG TTC TTC ACA AAC CAG GAT GTG CTG         672
Ser Val Leu Ser Ile Val Asp Trp Phe Phe Thr Asn Gln Asp Val Leu
210                 215                 220

CAG CCG TTT GCT GGC CCT GGC CAC TGG AAT GAC CCA GAC ATG CTC ATC         720
Gln Pro Phe Ala Gly Pro Gly His Trp Asn Asp Pro Asp Met Leu Ile
225                 230                 235                 240

ATT GGA AAT TTC GGT CTC AGC TAT GAG CAG TCA CGT TCC CAA ATG GCC         768
Ile Gly Asn Phe Gly Leu Ser Tyr Glu Gln Ser Arg Ser Gln Met Ala
                245                 250                 255

TTG TGG ACC ATT ATG GCA GCT CCA CTC CTC ATG TCC ACC GAC CTG CGC         816
Leu Trp Thr Ile Met Ala Ala Pro Leu Leu Met Ser Thr Asp Leu Arg
            260                 265                 270

ACT ATC TCG CCG AGT GCC AAG AAG ATT CTG CAG AAC CGC CTG ATG ATC         864
Thr Ile Ser Pro Ser Ala Lys Lys Ile Leu Gln Asn Arg Leu Met Ile
        275                 280                 285

CAG ATA AAC CAG GAC CCC TTG GGA ATC CAG GGG CGC AGG ATC ATC AAG         912
Gln Ile Asn Gln Asp Pro Leu Gly Ile Gln Gly Arg Arg Ile Ile Lys
290                 295                 300

GAG GGA TCC CAC ATT GAG GTG TTC CTG CGC CCG CTG TCA CAG GCT GCC         960
Glu Gly Ser His Ile Glu Val Phe Leu Arg Pro Leu Ser Gln Ala Ala
305                 310                 315                 320

AGT GCC CTG GTC TTC TTC AGC CGG AGG ACA GAC ATG CCC TTC CGC TAC        1008
Ser Ala Leu Val Phe Phe Ser Arg Arg Thr Asp Met Pro Phe Arg Tyr
                325                 330                 335

ACC ACC AGT CTT GCC AAG CTT GGC TTC CCC ATG GGA GCT GCA TAT GAG        1056
Thr Thr Ser Leu Ala Lys Leu Gly Phe Pro Met Gly Ala Ala Tyr Glu
            340                 345                 350

GTG CAA GAC GTG TAC AGT GGG AAG ATC ATC AGT GGC CTG AAG ACA GGG        1104
Val Gln Asp Val Tyr Ser Gly Lys Ile Ile Ser Gly Leu Lys Thr Gly
        355                 360                 365

GAC AAC TTC ACA GTG ATC ATC AAC CCC TCA GGG GTG GTG ATG TGG TAC        1152
Asp Asn Phe Thr Val Ile Ile Asn Pro Ser Gly Val Val Met Trp Tyr
370                 375                 380
```

```
CTG TGT CCC AAA GCA CTG CTC ATC CAG CAG CAA GCT CCT GGG GGG CCC      1200
Leu Cys Pro Lys Ala Leu Leu Ile Gln Gln Gln Ala Pro Gly Gly Pro
385             390                 395                 400

TCG CGC CTG CCC CTT CTG TGA GGC CCA TGA TTG GGA GCC CTG GGA TAC      1248
Ser Arg Leu Pro Leu Leu
                405

ATC TCA CCG CTG CTC AAG TGC CTT CTT CTG GTG TGG CTG GGG GAG GAC      1296

ATG CAG CTT GCT CCT CTG GCA CCA CCT GAT GAT TTC TAC TCA TTC CAC      1344

GTG AAG CAG GAC TTC TTG TTA CTC CCT CCT GAG AGC ATG CAA AGC GCT      1392

CTG AGG TCC TCC TGT GGA AGA GGA GTG TTC CCA GTG ACC ATC CTT TAG      1440

GAC CAG ATG TGG TCA CCT TTT TTC CTT TGC TTG GCT TAG GAC AAA GGG      1488

CTG TCC ACA GGC TGC ACC CCT CTT CCC AGG CAC CAT CCC CAG ACC AGG      1536

AGC TCC TGG GGC CAG GCT GTC TCT GTC TGG CAG CAG GAT CAG CAG GTA      1584

ACA CCA CTA CAG TGT AGT CCG CAC ATA ATG AAA AAG AAA TCT AAA CAA      1632

AAC GTG TGC CAG TAG TGT ACT GAA CCC GCT CTG GTT ACA GCA GAG CAA      1680

AAC CTG AGT TGT CCA TGC ACA ATC CCA GTA TCC TCA CTG TGG TGT TAG      1728

CAT GAA AAA TTG CAG TCA CAG TGC ATT GTG CAC GAG TGG TGT CTG GAA      1776

GAT GCT GAT GCT TGT TCG TGG TGG TCT TAA GGT GGG AGA TGC TCA TGG      1824

GTG CTG GCC AAG TTG CAT CTC AAT CTT GTG AGG CTG AAC CTT CCA GCA      1872

TTT CTC AGG GAA AGG CTC TTC CTT TTA AAG GCA GCC TGC ACA AAT AGA      1920

AGG GGC TCA GAA GGA CGC ACG AGG AGG GGC TCA GGT GGG CCG TGC TCC      1968

CCT GAC CAC CCC AAG AGG GGT CAA CTA CTC ACC AAA ATC TAC CCC TTT      2016

CAA GGC CAG GTC AGC CCA GGG AGA CGC ACC CAA GGT TAA ACC TCA AAA      2064

CAG GAA ATC ACC CTA TTT TAA ATT AGT GAG AAA TTG AAC TTC CCC ATT      2112

CTA TTC AGA TGA GGG CTA GAA GCC CAC TCT CCT TAG AAG GCA CGT GGT      2160

GGA TTC CTG CCC CTT GCA GAG ACA TTG TGG TCT GAA GCA AGA TGC TGA      2208

ATG TGA TCT TTG CAG CGC TGG AAA TGA CAT GTC TGT TTC ATG CTT GTG      2256

TGG GAG ATG GCT TTG TTT TTG TGA TTT TGA CAA TTT AAC TGA AAT AAA      2304

AGG GAA GCA GAG GGG                                                   2319
```

(2) INFORMATION FOR SEQ ID NO: 2:

(i) SEQUENCE CHARACTERISTICS:
        (A) LENGTH: 406
        (B) TYPE: amino acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (v) FRAGMENT TYPE:

(vi) ORIGINAL SOURCE:
        (A) ORGANISM: chicken liver
        (B) STRAIN:
        (C) INDIVIDUAL ISOLATE:
        (D) DEVELOPMENTAL STAGE:
        (E) HAPLOTYPE:

```
        (F) TISSUE TYPE:
        (G) CELL TYPE:
        (H) CELL LINE:
        (I) ORGANELLE:

(vii) IMMEDIATE SOURCE:    library (viii) POSITION IN GENOME:  unknown
        (A) CHROMOSOME/SEGMENT:
        (B) MAP POSITION:
        (C) UNITS:

(ix) FEATURE:
        (A) NAME/KEY:     chicken liver a-N-acetylgalactosaminidase
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:  2:

Met Leu Glu Asn Gly Leu Ala Arg Thr Pro Pro Met Gly Trp Leu Ala
 1               5                  10                  15

Trp Glu Arg Phe Arg Cys Asn Val Asn Cys Arg Glu Asp Pro Arg Gln
             20                  25                  30

Cys Ile Ser Glu Met Leu Phe Met Glu Met Ala Asp Arg Ile Ala Glu
         35                  40                  45

Asp Gly Trp Arg Glu Leu Gly Tyr Lys Tyr Ile Asn Ile Asp Asp Cys
     50                  55                  60

Trp Ala Ala Lys Gln Arg Asp Thr Glu Gly Arg Leu Val Pro Asp Pro
 65                  70                  75                  80

Glu Arg Phe Pro Arg Gly Ile Lys Ala Leu Ala Asp Tyr Val His Ala
                 85                  90                  95

Arg Gly Leu Lys Leu Gly Ile Tyr Gly Asp Leu Gly Arg Leu Thr Cys
            100                 105                 110

Gly Gly Tyr Pro Gly Thr Thr Leu Asp Arg Val Glu Gln Asp Ala Gln
            115                 120                 125

Thr Phe Ala Glu Trp Gly Val Asp Met Leu Lys Leu Asp Gly Cys Tyr
130                 135                 140

Ser Ser Gly Lys Glu Gln Ala Gln Gly Tyr Pro Gln Met Ala Arg Ala
145                 150                 155                 160

Leu Asn Ala Thr Gly Arg Pro Ile Val Tyr Ser Cys Ser Trp Pro Ala
                165                 170                 175

Tyr Gln Gly Gly Leu Pro Pro Lys Val Asn Tyr Thr Leu Leu Gly Glu
                180                 185                 190

Ile Cys Asn Leu Trp Arg Asn Tyr Asp Asp Ile Gln Asp Ser Trp Asp
            195                 200                 205

Ser Val Leu Ser Ile Val Asp Trp Phe Phe Thr Asn Gln Asp Val Leu
210                 215                 220

Gln Pro Phe Ala Gly Pro Gly His Trp Asn Asp Pro Asp Met Leu Ile
225                 230                 235                 240

Ile Gly Asn Phe Gly Leu Ser Tyr Glu Gln Ser Arg Ser Gln Met Ala
                245                 250                 255
```

-continued

```
Leu Trp Thr Ile Met Ala Ala Pro Leu Leu Met Ser Thr Asp Leu Arg
            260                 265                 270

Thr Ile Ser Pro Ser Ala Lys Lys Ile Leu Gln Asn Arg Leu Met Ile
        275                 280                 285

Gln Ile Asn Gln Asp Pro Leu Gly Ile Gln Gly Arg Arg Ile Ile Lys
    290                 295                 300

Glu Gly Ser His Ile Glu Val Phe Leu Arg Pro Leu Ser Gln Ala Ala
305                 310                 315                 320

Ser Ala Leu Val Phe Phe Ser Arg Arg Thr Asp Met Pro Phe Arg Tyr
                325                 330                 335

Thr Thr Ser Leu Ala Lys Leu Gly Phe Pro Met Gly Ala Ala Tyr Glu
            340                 345                 350

Val Gln Asp Val Tyr Ser Gly Lys Ile Ile Ser Gly Leu Lys Thr Gly
        355                 360                 365

Asp Asn Phe Thr Ile Val Ile Asn Pro Ser Gly Val Val Met Trp Tyr
    370                 375                 380

Leu Cys Pro Lys Ala Leu Leu Ile Gln Gln Gln Ala Pro Gly Gly Pro
385                 390                 395                 400

Ser Arg Leu Pro Leu Leu
                405

(2) INFORMATION FOR SEQ ID NO: 3:

(i) SEQUENCE CHARACTERISTICS:
        (A) LENGTH: 411
        (B) TYPE:  amino acid
        (C) STRANDEDNESS: double
        (D) TOPOLOGY:  linear (ii) MOLECULE TYPE:
        (A) DESCRIPTION:  cDNA to mRNA (iii) HYPOTHETICAL:    no (iv) ANTI-SENSE:      yes (v) FRAGMENT TYPE:

(vi) ORIGINAL SOURCE:
        (A) ORGANISM:   human
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:   library (viii) POSITION IN GENOME:  unknown
        (A) CHROMOSOME/SEGMENT:
        (B) MAP POSITION:
        (C) UNITS:

(ix) FEATURE:
        (A) NAME/KEY:   human a-N-acetylgalactosaminidase
        (B) LOCATION:
        (C) IDENTIFICATION METHOD:
        (D) OTHER INFORMATION:

(x) PUBLICATION INFORMATION:
        (A) AUTHORS: Wang et al
        (B) TITLE:  Human a-N-Acetylgalactosaminidase Molecular
            Cloning, Nucleotide Sequence, and Expression of a
            Full-Length cDNA
        (C) JOURNAL:  Journal of Biological Chemistry
```

```
          (D) VOLUME:  265
          (F) PAGES:   21859-21866
          (G) DATE:    1990
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:  3:

Met Leu Leu Lys Thr Val Leu Leu Gly His Val Ala Gln Val Leu
 1               5                  10                  15

Met Leu Asp Asn Gly Leu Leu Gln Thr Pro Met Gly Trp Leu Ala
                20                  25                  30

Trp Glu Arg Phe Arg Cys Asn Ile Asn Cys Asp Glu Asp Pro Lys Asn
                35                  40                  45

Cys Ile Ser Glu Gln Leu Phe Met Glu Met Ala Asp Arg Met Ala Gln
         50                  55                  60

Asp Gly Trp Arg Asp Met Gly Tyr Thr Tyr Leu Asn Ile Asp Asp Cys
 65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
                100                 105                 110

Gly Leu Lys Leu Gly Ile Tyr Ala Asp Met Gly Asn Phe Thr Cys Met
            115                 120                 125

Gly Tyr Pro Gly Thr Thr Leu Asp Lys Val Val Gln Asp Ala Gln Thr
        130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
                180                 185                 190

Glu Gly Gly Leu Pro Pro Arg Val Asn Tyr Ser Leu Leu Ala Asp Ile
            195                 200                 205

Cys Asn Leu Trp Arg Asn Tyr Asp Asp Ile Gln Asp Ser Trp Trp Ser
210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
        290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Ile Val Tyr Glu Ala
        355                 360                 365
```

```
Gln Asp Val Tyr Ser Gly Asp Ile Ile Ser Gly Leu Arg Asp Glu Thr
    370                 375                 380

Asn Phe Thr Ile Val Ile Asn Pro Ser Gly Val Val Met Trp Tyr Leu
385                 390                 395                 400

Tyr Pro Ile Lys Asn Leu Glu Met Ser Gln Gln
                405                 410

(2) INFORMATION FOR SEQ ID NO: 4:

(i) SEQUENCE CHARACTERISTICS:
         (A) LENGTH:  429
         (B) TYPE:    amino acid
         (C) STRANDEDNESS:  double
         (D) TOPOLOGY:   linear (ii) MOLECULE TYPE:
         (A) DESCRIPTION:  cDNA to mRNA (iii) HYPOTHETICAL:    no (iv) ANTI-SENSE:       yes (v) FRAGMENT TYPE:

(vi) ORIGINAL SOURCE:
         (A) ORGANISM:   human
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:    library (viii) POSITION IN GENOME:  unknown
         (A) CHROMOSOME/SEGMENT:
         (B) MAP POSITION:
         (C) UNITS:

(ix) FEATURE:
         (A) NAME/KEY:   human a-galactosidase
         (B) LOCATION:
         (C) IDENTIFICATION METHOD:
         (D) OTHER INFORMATION:

(x) PUBLICATION INFORMATION:
         (A) AUTHORS:  Calhoun et al
         (B) TITLE:  Fabry Disease:  Isolation of a cDNA Clone Encoding
             Human a-Galactosidase A
         (C) JOURNAL:    Proceedings of the National Academy of Science
             USA
         (D) VOLUME:  82
         (F) PAGES:  7364-7368
         (G) DATE:  1985
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO:   4:

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60
```

-continued

```
Ser Glu Lys Leu Phe Met Glu Met Ala Glu Leu Met Val Ser Glu Gly
 65                  70                  75                  80

Trp Lys Asp Ala Gly Tyr Glu Tyr Leu Cys Ile Asp Cys Trp Met
                 85                  90                  95

Ala Pro Gln Arg Asp Ser Glu Gly Arg Leu Gln Ala Asp Pro Gln Arg
                100                 105                 110

Phe Pro His Gly Ile Arg Gln Leu Ala Asn Tyr Val His Ser Lys Gly
            115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
                180                 185                 190

Arg Thr Gly Arg Ser Ile Val Tyr Ser Cys Glu Trp Pro Leu Tyr Met
            195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Ile Val Gly Asn
                260                 265                 270

Phe Gly Leu Ser Trp Asn Gln Gln Val Thr Gln Met Ala Leu Trp Ala
            275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Ile Val Ala Ile Asn
305                 310                 315                 320

Gln Asp Pro Leu Gly Lys Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
    355                 360                 365

Val Ala Ser Leu Gly Lys Gly Val Ala Cys Asn Pro Ala Cys Phe Ile
370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
                420                 425
```

(2) INFORMATION FOR SEQ ID NO: 5:

(i) SEQUENCE CHARACTERISTICS:
        (A) LENGTH: 438
        (B) TYPE: amino acid
        (C) STRANDEDNESS: double
        (D) TOPOLOGY: linear (ii) MOLECULE TYPE:

```
            (A) DESCRIPTION:  cDNA to mRNA (iii) HYPOTHETICAL:     no (iv) ANTI-SENSE:       yes (v) FRAGMENT TYPE:

(vi) ORIGINAL SOURCE:
            (A) ORGANISM:  yeast Saccharomyces cerevisiae
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:  library (viii) POSITION IN GENOME: unknown
            (A) CHROMOSOME/SEGMENT:
            (B) MAP POSITION:
            (C) UNITS:

(ix) FEATURE:
            (A) NAME/KEY:   yeast a-galactosidase (MEL1)
            (B) LOCATION:
            (C) IDENTIFICATION METHOD:
            (D) OTHER INFORMATION:

(x) PUBLICATION INFORMATION:
            (A) AUTHORS:  Liljestrom
            (B) TITLE:  The Nucleotide Sequence of the Yeast MEL1 Gene
            (C) JOURNAL:  Nucleic Acids Research
            (D) VOLUME:  13
            (F) PAGES:  7257-7268
            (G) DATE:  1985
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 5:

Met Phe Ala Phe Tyr Phe Leu Thr Ala Cys Ile Ser Leu Lys Gly Val
 1               5                  10                  15

Phe Gly Val Ser Pro Ser Tyr Asn Gly Leu Gly Leu Thr Pro Gln Met
                20                  25                  30

Gly Trp Asp Asn Trp Asn Thr Phe Ala Cys Asp Val Ser Glu Gln Leu
            35                  40                  45

Leu Leu Asp Thr Ala Asp Arg Ile Ser Asp Leu Gly Leu Lys Asp Met
        50                  55                  60

Gly Tyr Lys Tyr Ile Ile Leu Asp Asp Cys Trp Ser Ser Gly Arg Asp
65                  70                  75                  80

Ser Asp Gly Phe Leu Val Ala Asp Glu Gln Lys Phe Pro Asn Gly Met
                85                  90                  95

Gly His Val Ala Asp His Leu His Asn Asn Ser Phe Leu Phe Gly Met
            100                 105                 110

Tyr Ser Ser Ala Gly Glu Tyr Thr Cys Ala Gly Tyr Pro Gly Ser Leu
        115                 120                 125

Gly Arg Glu Glu Glu Asp Ala Gln Phe Phe Ala Asn Asn Arg Val Asp
    130                 135                 140

Tyr Leu Lys Tyr Asp Asn Cys Tyr Asn Lys Gly Gln Phe Gly Thr Pro
145                 150                 155                 160

Glu Ile Ser Tyr His Arg Tyr Lys Ala Met Ser Asp Ala Leu Asn Lys
                165                 170                 175
```

```
Thr Gly Arg Pro Ile Phe Tyr Ser Leu Cys Asn Trp Gly Gln Asp Leu
            180                 185                 190

Thr Phe Tyr Trp Gly Ser Gly Ile Ala Asn Ser Trp Arg Met Ser Gly
            195                 200                 205

Asp Val Thr Ala Glu Phe Thr Arg Pro Asp Ser Arg Cys Pro Cys Asp
            210                 215                 220

Gly Asp Glu Tyr Asp Cys Lys Tyr Ala Gly Phe His Cys Ser Ile Met
225                 230                 235                 240

Asn Ile Leu Asn Lys Ala Ala Pro Met Gly Gln Asn Ala Gly Val Gly
            245                 250                 255

Gly Trp Asn Asp Leu Asp Asn Leu Glu Val Gly Val Gly Asn Leu Thr
            260                 265                 270

Asp Asp Glu Glu Lys Ala His Phe Ser Met Trp Ala Met Val Lys Ser
            275                 280                 285

Pro Leu Ile Ile Gly Ala Asn Val Asn Asn Leu Lys Ala Ser Ser Tyr
            290                 295                 300

Ser Ile Tyr Ser Gln Ala Ser Ile Val Ala Ile Asn Gln Asp Ser Asn
305                 310                 315                 320

Gly Ile Pro Ala Thr Arg Val Trp Arg Tyr Tyr Val Ser Asp Thr Asp
            325                 330                 335

Glu Tyr Gly Gln Gly Glu Ile Gln Met Trp Ser Gly Pro Leu Asp Asn
            340                 345                 350

Gly Asp Gln Val Val Ala Leu Leu Asn Gly Gly Ser Val Ser Arg Pro
            355                 360                 365

Met Asn Thr Thr Leu Glu Glu Ile Phe Phe Asp Ser Asn Leu Gly Ser
            370                 375                 380

Lys Lys Leu Thr Ser Thr Trp Asp Ile Tyr Asp Leu Trp Ala Asn Arg
385                 390                 395                 400

Val Asp Asn Ser Thr Ala Ser Ala Ile Leu Gly Arg Asn Lys Thr Ala
            405                 410                 415

Thr Gly Ile Leu Tyr Asn Ala Thr Glu Gln Ser Tyr Lys Asp Gly Leu
            420                 425                 430

Ser Lys Asn Asp Thr Arg
            435
```

(2) INFORMATION FOR SEQ ID NO: 6:

(i) SEQUENCE CHARACTERISTICS:
        (A) LENGTH: 411
        (B) TYPE: amino acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (v) FRAGMENT TYPE:

(vi) ORIGINAL SOURCE:
        (A) ORGANISM: guar plant Cyamopsis tetragonoloba
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:    library (viii) POSITION IN GENOME:  unknown
         (A) CHROMOSOME/SEGMENT:
         (B) MAP POSITION:
         (C) UNITS:

(ix) FEATURE:
         (A) NAME/KEY:    guar a-galactosidase
         (B) LOCATION:
         (C) IDENTIFICATION METHOD:
         (D) OTHER INFORMATION:

(x) PUBLICATION INFORMATION:
         (A) AUTHORS:  Overbeeke et al
         (B) TITLE:  Cloning and Nucleotide Sequence of the
             a-Galactosidase cDNA From Cyamopsis tetragonoloba (guar)
         (C) JOURNAL:  Plant Molecular Biology
         (D) VOLUME:  13
         (F) PAGES:  541-550
         (G) DATE:  1989
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO:  6:

```
Met Ala Thr His Tyr Ser Ile Ile Gly Gly Met Ile Ile Val Val Leu
 1               5                  10                  15

Leu Met Ile Ile Gly Ser Glu Gly Gly Arg Leu Leu Glu Lys Lys Asn
             20                  25                  30

Arg Thr Ser Ala Glu Ala Glu His Tyr Asn Val Arg Arg Tyr Leu Ala
         35                  40                  45

Glu Asn Gly Leu Gly Gln Thr Pro Pro Met Gly Trp Asn Ser Trp Asn
 50                  55                  60

His Phe Gly Cys Asp Ile Asn Glu Asn Val Val Arg Glu Thr Ala Asp
65                  70                  75                  80

Ala Met Val Ser Thr Gly Leu Ala Ala Leu Gly Tyr Gln Tyr Ile Asn
                 85                  90                  95

Leu Asp Asp Cys Trp Ala Glu Leu Asn Arg Asp Ser Glu Gly Asn Met
            100                 105                 110

Val Pro Asn Ala Ala Phe Pro Ser Gly Ile Lys Ala Leu Ala Asp
        115                 120                 125

Tyr Val His Ser Lys Gly Leu Lys Leu Gly Val Tyr Ser Asp Ala Gly
        130                 135                 140

Asn Gln Thr Cys Ser Lys Arg Met Pro Gly Ser Leu Gly His Glu Glu
145                 150                 155                 160

Gln Asp Ala Lys Thr Phe Ala Ser Trp Gly Val Asp Tyr Leu Lys Tyr
                165                 170                 175

Asp Asn Cys Glu Asn Leu Gly Ile Ser Val Lys Glu Arg Tyr Pro Pro
            180                 185                 190

Met Gly Lys Ala Leu Leu Ser Ser Gly Arg Pro Ile Phe Phe Ser Met
        195                 200                 205

Cys Glu Trp Gly Trp Glu Asp Pro Gln Ile Trp Ala Lys Ser Ile Gly
    210                 215                 220

Asn Ser Trp Arg Thr Thr Gly Asp Ile Glu Asp Asn Trp Asn Ser Met
225                 230                 235                 240

Thr Ser Ile Ala Asp Ser Asn Asp Lys Trp Ala Ser Tyr Ala Gly Pro
                245                 250                 255

Gly Gly Trp Asn Asp Pro Asp Met Leu Glu Val Gly Asn Gly Gly Met
            260                 265                 270
```

```
Thr Thr Glu Glu Tyr Arg Ser His Phe Ser Ile Trp Ala Leu Ala Lys
        275                 280                 285

Ala Pro Leu Leu Val Gly Cys Asp Ile Arg Ala Met Asp Asp Thr Thr
        290                 295                 300

His Glu Leu Ile Ser Asn Ala Glu Ile Val Ala Val Asn Gln Asp Lys
305                 310                 315                 320

Leu Gly Val Gln Gly Lys Lys Val Lys Ser Thr Asn Asp Leu Glu Val
                325                 330                 335

Trp Ala Gly Pro Leu Ser Asp Asn Lys Val Ala Val Ile Leu Trp Asn
                340                 345                 350

Arg Ser Ser Arg Ala Thr Val Thr Ala Ser Trp Ser Asp Ile Gly
        355                 360                 365

Leu Gln Gln Gly Thr Thr Val Asp Ala Arg Asp Leu Trp Glu His Ser
    370                 375                 380

Thr Gln Ser Leu Val Ser Gly Glu Ile Ser Ala Glu Ile Asp Ser His
385                 390                 395                 400

Ala Cys Lys Met Tyr Val Leu Thr Pro Arg Ser
                405                 410

(2) INFORMATION FOR SEQ ID NO: 7:

(i) SEQUENCE CHARACTERISTICS:
        (A) LENGTH:   447
        (B) TYPE:     amino acid
        (C) STRANDEDNESS:  double
        (D) TOPOLOGY:   linear (ii) MOLECULE TYPE:
        (A) DESCRIPTION:  cDNA to mRNA (iii) HYPOTHETICAL:    no (iv) ANTI-SENSE:      yes (v) FRAGMENT TYPE:

(vi) ORIGINAL SOURCE:
        (A) ORGANISM:  Aspergillis niger
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:   library (viii) POSITION IN GENOME:  unknown
        (A) CHROMOSOME/SEGMENT:
        (B) MAP POSITION:
        (C) UNITS:

(ix) FEATURE:
        (A) NAME/KEY:   Aspergillus niger a-galactosidase
        (B) LOCATION:
        (C) IDENTIFICATION METHOD:
        (D) OTHER INFORMATION:

(x) PUBLICATION INFORMATION:
        (A) AUTHORS:  den Herder et al
        (B) TITLE:  Cloning and Expression of a Member of the
            Aspergillus niger Gene Family Encoding a-Galactosidase
        (C) JOURNAL:  Molecular and General Genetics
        (D) VOLUME:  233
        (F) PAGES:  404-410
        (G) DATE:  1992
        (H) DOCUMENT NUMBER:
```

(I) FILING DATE:
(J) PUBLICATION DATE:
(K) RELEVANT RESIDUES IN SEQ ID NO:

(xi) SEQUENCE DESCRIPTION: SEQ ID NO: 7:

```
Met Ile Gln Gly Leu Glu Ser Ile Met Asn Gln Thr Lys Arg Ile
1               5                   10                  15

Leu Leu Ala Ala Thr Leu Ala Ala Thr Pro Trp Gln Val Tyr Gly Ser
                20                  25                  30

Ile Glu Gln Pro Ser Leu Leu Pro Thr Pro Pro Met Gly Pro Asn Asn
                35                  40                  45

Trp Ala Arg Phe Met Cys Asp Leu Asn Glu Thr Leu Phe Thr Glu Thr
        50                  55                  60

Ala Asp Thr Met Ala Ala Asn Gly Leu Arg Asp Ala Gly Tyr Asn Arg
65                  70                  75                  80

Ile Asn Leu Asp Asp Cys Trp Met Ala Tyr Gln Arg Ser Asp Asn Gly
                85                  90                  95

Ser Leu Gln Trp Asn Thr Thr Lys Phe Pro His Gly Leu Pro Trp Leu
                100                 105                 110

Ala Lys Tyr Val Lys Ala Lys Gly Phe His Phe Gly Ile Tyr Glu Asp
                115                 120                 125

Ser Gly Asn Met Thr Cys Gly Gly Tyr Pro Gly Ser Tyr Asn His Glu
130                 135                 140

Glu Gln Asp Ala Asn Thr Phe Ala Ser Trp Gly Ile Asp Tyr Leu Lys
145                 150                 155                 160

Leu Asp Gly Cys Asn Val Tyr Ala Thr Gln Gly Arg Thr Leu Glu Glu
                165                 170                 175

Glu Tyr Lys Gln Arg Tyr Gly His Trp His Gln Val Leu Ser Lys Met
                180                 185                 190

Gln His Pro Leu Ile Phe Ser Glu Ser Ala Pro Ala Tyr Phe Ala Gly
                195                 200                 205

Thr Asp Asn Asn Thr Asp Trp Tyr Thr Val Met Asp Trp Val Pro Ile
210                 215                 220

Tyr Gly Glu Leu Ala Arg His Ser Thr Asp Ile Leu Val Tyr Ser Gly
225                 230                 235                 240

Ala Gly Ser Ala Trp Asp Ser Ile Met Asn Asn Tyr Asn Tyr Asn Thr
                245                 250                 255

Leu Leu Ala Arg Tyr Gln Arg Pro Gly Tyr Phe Asn Asp Pro Asp Phe
                260                 265                 270

Leu Ile Pro Asp His Pro Gly Leu Thr Ala Asp Glu Lys Arg Ser His
                275                 280                 285

Phe Ala Leu Trp Ala Ser Phe Ser Ala Pro Leu Ile Ile Ser Ala Tyr
                290                 295                 300

Ile Pro Ala Leu Ser Lys Asp Glu Ile Ala Phe Leu Ile Asn Glu Ala
305                 310                 315                 320

Leu Ile Ala Val Asn Gln Asp Pro Leu Ala Gln Gln Ala Thr Leu Ala
                325                 330                 335

Ser Arg Asp Asp Thr Leu Asp Ile Leu Thr Arg Ser Leu Ala Asn Gly
                340                 345                 350

Asp Arg Leu Leu Thr Val Leu Asn Lys Gly Asn Thr Thr Val Thr Arg
                355                 360                 365

Asp Ile Pro Val Gln Trp Leu Gly Leu Thr Glu Thr Asp Cys Thr Tyr
                370                 375                 380

Thr Ala Glu Asp Leu Trp Asp Gly Lys Thr Gln Lys Ile Ser Asp His
```

```
-continued 385                   390                   395                   400

Ile Lys Ile Glu Leu Ala Ser His Ala Thr Ala Val Phe Arg Leu Ser
                405                 410                 415

Leu Pro Gln Gly Cys Ser Ser Val Val Pro Thr Gly Leu Val Phe Asn
                420                 425                 430

Thr Ala Ser Gly Asn Cys Leu Thr Ala Ala Ser Asn Ser Ser Val
                435                 440                 445
```